United States Patent
Whitaker et al.

(10) Patent No.: US 12,016,316 B2
(45) Date of Patent: Jun. 25, 2024

(54) APPARATUS AND METHODS FOR PRODUCTION OF DIPTERAN INSECTS

(71) Applicant: ENTOCYCLE LTD, London (GB)

(72) Inventors: Keiran Camilo Olivares Whitaker, London (GB); Paul Samuel Hillmann, London (GB)

(73) Assignee: Entocycle Ltd, London (GB)

( * ) Notice: Subject to any disclaimer, the term of this patent is extended or adjusted under 35 U.S.C. 154(b) by 417 days.

(21) Appl. No.: 16/647,356

(22) PCT Filed: Sep. 14, 2018

(86) PCT No.: PCT/GB2018/052631
§ 371 (c)(1),
(2) Date: Mar. 13, 2020

(87) PCT Pub. No.: WO2019/053456
PCT Pub. Date: Mar. 21, 2019

(65) Prior Publication Data
US 2020/0281176 A1    Sep. 10, 2020

(30) Foreign Application Priority Data
Sep. 14, 2017   (GB) .................................... 1714822

(51) Int. Cl.
*A01K 67/033*   (2006.01)
(52) U.S. Cl.
CPC ...... *A01K 67/033* (2013.01); *A01K 2227/706* (2013.01)
(58) Field of Classification Search
CPC ................ A01K 67/033; A01K 2227/706
See application file for complete search history.

(56) References Cited

U.S. PATENT DOCUMENTS

| | | | | |
|---|---|---|---|---|
| 1,974,549 A | * | 9/1934 | Spencer | A01K 67/033 |
| | | | | 119/6.5 |
| 2,539,633 A | * | 1/1951 | Morrill | A01K 67/033 |
| | | | | 43/118 |

(Continued)

FOREIGN PATENT DOCUMENTS

| EP | 2 703 372 A1 | 3/2014 |
|---|---|---|
| FR | 3 013 561 A1 | 5/2015 |

(Continued)

OTHER PUBLICATIONS

International Search Report and Written Opinion for International Application No. PCT/GB2018/052631, dated Dec. 6, 2018, 15 pages.

(Continued)

*Primary Examiner* — Monica L Perry
*Assistant Examiner* — Aaron M Rodziwicz
(74) *Attorney, Agent, or Firm* — COOLEY LLP

(57) ABSTRACT

A modular system for breeding and harvesting flies, comprising: an egg-growth chamber configured to receive fertilised eggs and to permit the fertilised eggs to develop and hatch as larvae, the egg-growth chamber comprising at least one egg holder, the or each egg holder being adapted to retain the fertilized eggs and allow passage of the larvae from the egg-holder to a food source to provide larvae in the food source; a larval chamber configured to receive the larvae in the food source and to permit the larvae to feed on the food source and develop into pre-pupae to provide pre-pupae in the food source; a pupation chamber configured to receive the pre-pupae in the food source and to permit the pre-pupae to develop into pupae, the pupation chamber being configured to dry the food source and the pre-pupae to provide pupae in a dried food source; a release box configured to receive the pupae in the dried food source and to permit the pupae to develop into adult flies, the release box (Continued)

comprising one or more outlets for adult flies to leave the release box; and a breeding chamber configured to receive adult flies via the one or more outlets in the release box and to permit adult flies to mate to provide gravid females, and wherein the gravid females oviposit fertilised eggs in one or more ovipositing racks. Methods and apparatus for breeding flies and apparatus for counting flies and larvae are also disclosed.

24 Claims, 4 Drawing Sheets

(56) References Cited

U.S. PATENT DOCUMENTS

| | | | | |
|---|---|---|---|---|
| 4,411,220 A * | 10/1983 | Voegele | ............... | A01K 67/033 |
| | | | | 119/6.6 |
| 5,351,643 A * | 10/1994 | Hughes | ............... | A01K 67/033 |
| | | | | 119/6.5 |
| 5,594,654 A | 1/1997 | Shuman et al. | | |
| 6,863,022 B2 * | 3/2005 | Fleischmann | ........ | A01K 1/0236 |
| | | | | 119/6.5 |
| 9,462,795 B2 * | 10/2016 | Chin | ............... | A01K 67/033 |
| 9,642,344 B2 * | 5/2017 | Unger | ............... | A01K 67/033 |
| 10,278,368 B1 * | 5/2019 | Peeters | ............... | A01K 1/031 |
| 10,306,875 B1 * | 6/2019 | Massaro | ............... | A01K 67/033 |
| 10,362,772 B2 * | 7/2019 | Arsiwalla | ............... | A01K 67/033 |
| 10,405,528 B2 * | 9/2019 | Comparat | ............... | B65G 1/0407 |
| 10,667,502 B2 * | 6/2020 | Wu | ............... | A01K 67/033 |
| 10,779,521 B2 * | 9/2020 | Massaro | ............... | G06Q 50/02 |
| 10,842,138 B1 * | 11/2020 | Lolley | ............... | A01K 67/033 |
| 2008/0087231 A1 * | 4/2008 | Gabriel | ............... | A01K 1/031 |
| | | | | 119/455 |
| 2011/0174222 A1 | 7/2011 | Lee | | |
| 2013/0319334 A1 * | 12/2013 | Newton | ............... | A01K 67/033 |
| | | | | 119/51.01 |
| 2014/0020630 A1 * | 1/2014 | Courtright | ............ | A01K 67/033 |
| | | | | 119/6.6 |
| 2015/0122182 A1 * | 5/2015 | Aldana | ............... | A01K 67/033 |
| | | | | 119/6.6 |
| 2015/0296760 A1 * | 10/2015 | Perednia | ............ | A01K 67/033 |
| | | | | 119/6.5 |
| 2016/0066552 A1 * | 3/2016 | Arsiwalla | ............ | A01K 1/0047 |
| | | | | 119/6.5 |
| 2019/0387704 A1 * | 12/2019 | Hall | ............... | B65G 47/248 |

FOREIGN PATENT DOCUMENTS

| | | |
|---|---|---|
| GB | 2 110 516 A | 6/1983 |
| WO | WO 2013/166590 A1 | 11/2013 |
| WO | WO 2016/011541 A1 | 1/2016 |
| WO | WO 2019/053456 A1 | 3/2019 |

OTHER PUBLICATIONS

International Preliminary Report on Patentability for International Application No. PCT/GB2018/052631, dated Mar. 17, 2020, 10 pages.

* cited by examiner

APPARATUS AND METHODS FOR PRODUCTION OF DIPTERAN INSECTS

CROSS-REFERENCES TO RELATED APPLICATIONS

This application is a U.S. national phase application of International PCT Patent Application No. PCT/GB2018/052631, which was filed on Sep. 14, 2018, which claims priority to GB Patent Application No. 1714822.2, filed Sep. 14, 2017. These applications are incorporated herein by reference in their entireties.

FIELD OF THE INVENTION

The present invention relates to breeding of an insect population, in particular a fly population. Especially, optimisation and control of the breeding cycle is addressed to enable flies at the larval stage to be produced and harvested and for a population of flies to be maintained for breeding to provide following generations. In this way a closed cycle of production is achieved.

BACKGROUND

Insects have been relied on as a source of food for millennia. Insects provide a valuable source of protein, fibre and are also a useful source of many vitamins and minerals. Over recent years there has been growing interest in the field of breeding insects for human and animal consumption. The intentional cultivation of insects, sometimes referred to as 'insect farming', has been suggested as one promising way to provide future food security for the ever-increasing population of the world.

Insects can convert plant material to food approximately 10-fold more efficiently than traditionally reared food-producing animals such as pigs and cows. Insects also require far less land and water to sustain growth. Breeding insects has an energy input to protein output ratio of around 4:1 whereas traditional raised livestock has a ratio of 54:1.

Despite the clear advantages of the use of insects as a food source it has historically formed only a small part of the food intake of humans and animals in most countries, particularly in developed countries. While this is partly due to cultural reluctance to change to food from insect sources, this is also largely due to the difficulties and limited understanding of how to farm insects on an industrial scale. While each insect is different, and has differing environmental and nutritional requirements, for the major food producing insects these are becoming understood. What remains a challenge for the industry is how to develop robust, reproducible breeding routines with minimal or no manual operator input that are scalable for use in an industrial scale.

Dipteran insects, more commonly known as 'flies' are particularly useful in insect farming due to their rapid lifecycle. The Black Soldier Fly (BSF), or *Hermetia illucens* in particular is known in the art as being efficient at digesting waste organic material and converting this, as part of its growth, into protein and other nutrients suitable for consumption by animals, including humans.

Black soldier flies have several advantages over other insects that make them particularly well adapted for farming. Firstly, they are highly efficient at digesting; it is reported that a gram of black soldier fly eggs can convert to the equivalent of 2.4 kg of protein in eighteen days. Secondly, the flying adults do not have mouth parts so do not bite, neither do they sting. Thirdly, they are not attracted to human foodstuffs so are less likely to function as a vector for diseases picked up from other sources. Attempts have been made to breed black soldier flies and some, limited, success has been had. However, the equipment used and the methods described do not provide a means for scaling black soldier fly production suitable for commercial scale production.

SUMMARY

The present invention seeks to improve the apparatus and methodology currently in use for the breeding and/or farming of fly larvae.

In a first aspect, the invention provides a modular system for breeding flies, comprising:
  an egg-growth chamber configured to receive fertilised eggs and to permit the fertilised eggs to develop and hatch as larvae, the egg-growth chamber comprising at least one egg holder, the or each egg holder being adapted to retain the fertilized eggs and allow passage of the larvae from the egg-holder to a food source to provide larvae in the food source;
  a larval chamber configured to receive the larvae in the food source and to permit the larvae to feed on the food source and develop into pre-pupae to provide pre-pupae in the food source;
  a pupation chamber configured to receive the pre-pupae in the food source and to permit the pre-pupae to develop into pupae, the pupation chamber being configured to dry the food source and the pre-pupae to provide pupae in a dried food source;
  a release box configured to receive the pupae in the dried food source and to permit the pupae to develop into adult flies, the release box comprising one or more outlets for adult flies to leave the release box; and
  a breeding chamber configured to receive adult flies via the one or more outlets in the release box and to permit adult flies to mate to provide gravid females, and wherein the gravid females oviposit fertilised eggs in one or more ovipositing racks.

In a second aspect, the invention provides a process for breeding flies, comprising the steps of:
  a) providing at least one fertilised egg to at least one egg holder in an egg-growth chamber, the or each egg holder being adapted to retain the at least one fertilized egg and allow passage of the larvae therefrom after hatching;
  b) providing conditions within the egg-growth chamber suitable for the fertilized egg to hatch as larvae wherein after hatching the larvae pass from the egg holder to a food source to provide larvae in the food source;
  c) placing the larvae in the food source in a larval chamber and allowing the larvae to grow and transform into pre-pupae in the food source;
  d) placing the pre-pupae in the food source in a pupation chamber, the pupation chamber being configured to dry the pre-pupae in the food source to provide pupae in a dried food source;
  e) placing the pupae in the dried food source in a release box in which the pupae develop into adult flies, the release box comprising one or more outlets for adult flies to leave the release box;
  f) allowing at least one male adult fly and at least one female adult fly to leave the release box into a breeding chamber;
  g) allowing at least one male adult fly and at least one female adult fly to mate to provide at least one gravid female, wherein the at least one gravid female oviposits at least one fertilised egg in one or more ovipositing racks;

f) removing at least one fertilised egg from the one or more ovipositing racks;

g) optionally, repeating steps (a) to (f).

A third aspect of the invention provides a modular system for breeding flies, comprising:

an egg-growth chamber in which fertilised eggs develop and hatch as larvae, the egg-growth chamber comprising at least one egg holder, the or each egg holder being adapted to retain the fertilized eggs and allow passage of the larvae therefrom after hatching, wherein the egg-growth chamber further comprises a means to count the larvae passing from the egg holder;

a larval chamber configured to receive the larvae in a food source and to permit the larvae to feed on the food source and develop into pre-pupae;

a pupation chamber configured to receive the pre-pupae and to permit the pre-pupae to develop into pupae;

a release box configured to receive pupae and permit the pupae to develop into adult flies, the release box comprising one or more outlets for adult flies; and a breeding chamber configured to receive adult flies via the outlets in the release box and to permit the adult flies to mate to provide at least one gravid female which oviposits fertilised eggs in one or more ovipositing racks.

A fourth aspect of the invention provides a process for breeding flies, comprising the steps of:

a) providing at least one fertilised egg to at least one egg holder in an egg-growth chamber, the or each egg holder being adapted to retain the at least one fertilized egg and allow passage of the larvae therefrom after hatching;

b) providing conditions within the egg-growth chamber suitable for the fertilized egg to hatch as larvae wherein after hatching the larvae pass from the egg holder to a food source;

c) allowing the larvae to pass from the egg holder to contact a surface configured to separate the larvae into individual larvae;

d) counting the individual larvae directed from the surface using a monitoring device;

e) providing a pre-determined number of counted larvae to a food source;

f) placing the pre-determined number of counted larvae in a food source in a larval chamber and allowing the larvae to grow and transform into pre-pupae;

g) placing the pre-pupae to a pupation chamber and allowing the pre-pupae to transform into pupae;

h) placing the pupae to a release box in which the pupae develop into adult flies, the release box comprising one or more outlets for adult flies to leave the release box;

i) allowing at least one male adult fly and at least one female adult fly to leave the release box into a breeding chamber;

j) allowing at least one male adult fly and at least one female adult fly to mate to provide at least one gravid female, wherein the at least one gravid female oviposits at least one fertilised egg in one or more removable ovipositing racks;

k) removing at least one fertilised egg from the one or more ovipositing racks;

l) optionally, repeating steps (a) to (k).

A fifth aspect of the invention provides an apparatus for counting larvae emerging from fertilized eggs of a fly, the system comprising:

a drop point from where larvae hatching from at least one fertilised egg falls;

one or more angled surfaces positioned below the drop point such that as the larvae fall from the drop point they contact at least one of the one or more angled surfaces, wherein said contact separates the larvae into individuals and directs the individual larvae from the one or more angled surfaces;

wherein a monitoring device counts the individual larvae directed from the one or more surfaces.

In a sixth aspect the invention provides a method for counting larvae comprising the steps of:

Providing one or more fertilised eggs;

Providing conditions suitable to allow the eggs to hatch as larvae; and

Counting the larvae as after they emerge from the one or more fertilised eggs.

In an embodiment, the method comprises use of the apparatus of the fifth aspect of the invention.

In a seventh aspect the invention provides a release box in which the pupae develop into adult flies, the release box comprising:

at least one discrete position for receiving pupae;

one or more outlets for adult flies to leave the release box;

wherein the or each outlet comprises a monitoring device for counting the individual flies leaving the release box.

In an eighth embodiment the invention provides a method of counting flies entering a breeding chamber, wherein said method comprises:

Providing pupae in a pupation chamber in one or more containers, wherein the or each one or more containers comprises one or more outlets configured to allow adult flies to pass from the release box to the breeding chamber;

Counting flies as they pass through the one or more outlets.

In an embodiment, the method comprises use of the apparatus of the eighth aspect of the invention.

BRIEF DESCRIPTION OF THE DRAWINGS

The invention is described with reference to the accompanying drawing which illustrates by way of example only, an embodiment of the breeding methodology. In the drawings.

DETAILED DESCRIPTION

Figure 1:
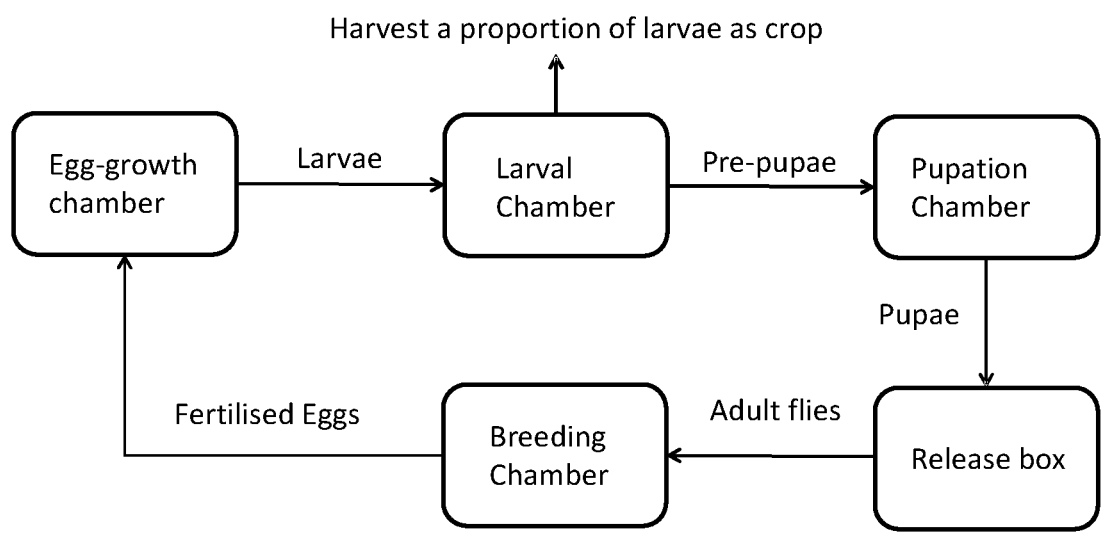
FIG. 1 shows a schematic of the apparatus of an embodiment of the present invention.

Those skilled in the art will be aware that the present disclosure is subject to variations and modifications other than those specifically described. It is to be understood that the present disclosure includes all such variations and modifications. The disclosure also includes all such steps, features, compositions, and compounds referred to or indicated in this specification, individually or collectively, and any and all combinations of any or more of such steps or features.

For convenience, before further description of the present disclosure, certain terms employed in the specification, and examples are delineated here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles 'a', 'an' and 'the' are used to refer to one or to more than one (i.e. to at least one) of the grammatical object of the article.

As used herein, the term 'comprising' means any of the recited elements are necessarily included and other elements may optionally be included as well. 'Consisting essentially of' means any recited elements are necessarily included, elements which would materially affect the basic and novel characteristics of the listed elements are excluded, and other elements may optionally be included. 'Consisting of' means that all elements other than those listed are excluded. Embodiments defined by each of these terms are within the scope of this invention.

As used herein, the term 'oviposit' or 'ovipositing' refers to laying of eggs, in particular by an insect. Female insects tend to have ovipositing tubes through which fertilised eggs are laid.

As used herein, the term 'gravid female' refers to a female carrying fertilised eggs.

As used herein, the term 'pre-pupae' refers to an intermediate stage of development between the larval stage and the pupae stage. In the stage the exoskeleton of the larvae has begun to harden and darken but the larvae still moves and/or feeds. It is to be understood that there is no strict transition from larvae to pre-pupae to pupae, or indeed, larvae to pupae, and the term pre-pupae may in some circumstances be used interchangeably herein or I the literature with the term larvae, for example late-stage larvae, or pupae, for example early stage pupae, depending on the given stage of development.

As used herein, each of the terms 'eggs', 'larvae', 'pre-pupae', 'pupae' and 'flies' refers to the bulk of the batch referred to. It will be understood that due to natural variation and mixing of batches of different ages, each batch may include minor proportions of developmental stages before and/or after that of the bulk of the batch, for example, pre-pupae may mean a bulk batch of pre-pupae including minor proportions of larvae and pupae or adult flies.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods, and materials are now described. All publications mentioned herein are incorporated herein by reference.

The invention described herein relates to methods and apparatus for breeding dipteran insects, in particular, the black soldier fly (BSF). The lifecycle of the BSF, as with most insects, can be split into several discrete stages: egg, larva, pre-pupa, pupa and adult. Pre-pupa is not universally accepted as a separate stage, but is often regarded as a transitional form. However, herein it is included for convenience as a separate stage. For each of these stages, there is an expected duration, which depends on the particular conditions in which the BSF finds itself. Under controlled conditions however, while the duration of a lifespan can still be subject to natural variation for individuals, for statistically large numbers the distribution of duration can be well represented by a standard bell-shaped curve. This facet underlies the principle of the current invention to provide a semi-continuous batch process for the production of larvae, and also to provide sufficient eggs to enable future generations of flies to be produced to keep the process in continuation. The invention can utilise or combine populations, at different stages of development under different bell-shaped curves, into single batches that may be progressed as one. With this approach those reaching the end of the stage can be removed, being replaced by individuals at the beginning of the stage. The invention therefore additionally contemplates means of optimising various process stages for ease of production and reduced operator input. It has been found that it can also be important to have various points in the process at which measurements are taken to determine and control how many individuals are present or how many individuals have moved from one stage to the next. Methods and devices for obtaining this information are therefore also disclosed.

FIG. 1 shows schematic of the apparatus of an embodiment of the present invention. In this embodiment, the apparatus comprises five stages or chambers: namely an egg-growth chamber, a larval chamber, a pupation chamber, a release box and a breeding chamber. The egg-growth chamber is where fertilised eggs are incubated to hatch as larvae. The larval chamber is where the larvae grow and mature into pre-pupae. The pupation chamber is where the pre-pupae develop into pupae. The release box is where the pupae emerge as adult flies to be released into the breeding chamber where the adult flies mate and the gravid females oviposit their fertilised eggs which are then returned to the egg-growth chamber.

As is apparent, fertilised eggs laid in the breeding chamber are transferred to the egg-growth chamber to provide a cyclical process. Dealing initially therefore with what is termed herein as the first stage namely the egg-growth, or egg-hatching, stage, it should be noted that the term "first" is merely a suitable label for a starting point on the cycle and not an absolute term in this context.

For the first stage of the process an egg-growth chamber is provided. In overview, the egg-growth chamber provides one or more suitable locations in which one or more fertilised eggs may be retained and incubated under suitable environmental conditions, and the emerging larvae collected. In an embodiment, the location(s) in which fertilised eggs are retained are denoted egg holders, and may be alternatively denoted as egg platforms, egg cages, egg trays, hatching trays, hatching platforms or hatching distribution platforms.

In an embodiment, the egg holders are configured to retain fertilised eggs and allow emerging larvae to migrate therefrom. Any means of allowing the larvae to migrate from the egg holders is contemplated. Suitably, the means of allowing the larvae to migrate may be an open topped tray with no or low rising side walls that allow the larvae to crawl over the side. Alternatively, the egg holder may have a perforated base or walls wherein the perforations are sized to retain fertilised eggs and allow the passage of newly hatched larvae. Suitably, the perforations may have a diameter in the range of 0.5 mm to 3 mm. In embodiments, the egg holders may encase the fertilised eggs, for example as a box or cage. Suitably, the egg holders are formed of a surface or plate with no cover. This has advantages in terms of ease of access and visual monitoring.

The environmental conditions in the egg-growth chamber are suitable for incubation of the fertilised eggs. Suitably at least the temperature and relative humidity are controlled to provide suitable environmental conditions. Suitably the temperature and relative humidity are controlled to be above that of the ambient air. Suitably the temperature of the egg-growth chamber may be at least 25° C. More suitably the temperature may be at least 26° C., 27° C., 28° C., 29° C. or 30° C. The temperature may be at most 35° C. More suitably the temperature is at most 34° C., 33° C., 32° C., 31° C., 30° C., 29° C. or 28° C. Suitably, the temperature may be in the range of 25° C. to 35° C. More suitably the temperature may be in the range of 26° C. to 32° C. Most suitably the temperature may be in the range of 26° C. to 30° C.

Suitably the relative humidity in the larval chamber is at least 50%. Suitably the relative humidity is above 65%. The relative humidity may be above 66%, 67%, 68%, 69%, 70%, 71%, 72%, 73%, 74% or 75%. The relative humidity may be a most 80%. The relative humidity may be at most 79%, 78%, 77%, 76%, 75%, 74%, 73%, 72%, 71%. 70%, 69%, 68%, 67%, 66% or 65%. Suitably the relative humidity may be in the range from 60% to 80%. More suitably the relative humidity may be in the range of from 65% to 75%. The relative humidity may be measured using known techniques with a psychrometer or a hygrometer.

Determination of the growth stage of the eggs/larvae can be made manually, by observation of the state of the eggs/larvae by an operator. Alternatively, chemical sensing of the air above the eggs can be carried out, utilising any suitable sensor to determine the chemicals being produced by the eggs and to match this against the composition known to be produced close to the point when an egg hatches. Suitable sensing may comprise collection of a sample of the air above or surrounding the incubating eggs and feeding this to a suitable detector, such as a Gas Chromatography Mass Spectral (GC/MS) analyser or high performance liquid chromatography (HPLC) analyser which can allow identification of chemicals of interest by their molecular mass. An optical monitoring device, such as a camera may also be used to allow an operator to observe the eggs/larvae or some other form of identification/colour analysis of the ageing eggs. The use of a sensor allows automation of this aspect of the process and obviates the need for the regular presence of an operator.

In embodiments, one or more egg holders are provided. Suitably more than one egg holder is provided. More suitably a series of a plurality of egg holders is provided. In embodiments when a series of a plurality of egg holders is provided, fertilised eggs may be added in chronological sequence starting from one egg holder at an earliest time point and then adding fertilised eggs from a later time point to a next and then subsequent egg holders. Fertilised eggs from different, but closely related time points, for example between 1 to 3 days, or 1 to 2 days, of from different batches on the same day, may be combined on a single egg holder.

Once a suitable time period has elapsed such that all or the majority of the eggs on a holder have hatched, that egg holder is removed and disposed of or cleaned ready for re-use. In embodiments, the timing of removal is based on the expected incubation period for the fertilised eggs based on the bell-shape distribution for the species, Alternatively, the timing for removal is based on a visual inspection or other means of monitoring the hatching state of the fertilised eggs as detailed above.

In embodiments, the larvae passing from the egg holders are captured. In embodiments, the larvae may be captured in any suitable container or on a suitable surface. Suitably, the larvae are captured in a container or on a surface where a food source is present. Suitably, the container may be a tray, cup, crate or other receptacle that can retain the larvae and the food source. In embodiments where the larvae are captured on a surface, the surface may be a conveyor, such as a conveyor belt, that transfers the larvae between the chambers of the apparatus or transfers the larvae to another container or surface. Suitably, the same container or surface may be used to transfer the larvae, and the pre-pupae and/or pupae that mature therefrom, through the larval chamber, pupation chamber and to the release box without transfer of the contents.

The food source can be any suitable material for sustaining larvae. Suitably, the food source may be food waste and/or detritus material. Examples of food source may be brewer's grains, coffee grains, vegetable matter or combinations thereof.

In embodiments, between passing from the egg holder to the container or surface on which the larvae are captured, the larvae are separated and/or counted. Counting the number of individual larvae is important for ensuring that the concentration of larvae, and pre-pupae and/or pupae that mature therefrom, in the food source is optimal to ensure that sufficient food is available, yet not too much that would lead to waste. Accurate monitoring of numbers of larvae also offers a means of batch control which is important for the efficiency of an industrial process. Due to the statistical averaging of the amount of food required by larvae, accurate monitoring of the number of larvae captured in a single container, or on an area of surface is also important for standardising procedures for the addition of further food, if required, during the larval maturation process.

Larvae passing from the egg holder can be separate individuals or can combine in groups comprising two or more larvae. The counting of larvae is complicated by this grouping of individuals (so called 'multis') as most monitoring equipment is typically not able to distinguish these from individuals leading to mis-counting events. It is therefore important to take steps to separate at least the majority of the muftis into individual larvae prior to counting.

In embodiments of the present invention, the larvae are passed through a system for separating multiple groups of larvae. The means of separating larvae is not restricted. Suitably, the larvae that have passed from the egg holders are impacted on a surface with sufficient force to cause groups of larvae to separate into individuals while preventing injury to the larvae. Suitably, the larvae are dropped from a drop-point onto a surface from a given height. It has been found that both the height of the drop and the angle of incidence at which the larvae strike the surface with respect to the vertical drop direction is important for ensuring a high success rate in separation of the larvae into individuals. Suitably, the height of the drop is at least 100 mm. More suitably the height of the drop is 90 mm, 80 mm, 70 mm, 60 mm, 50 mm or 40 mm. Suitably, the height of the drop is less than 400 mm. More suitably, the height of the drop is less than 350 mm, 300 mm, 250 mm, 200 mm, 190 mm, 180 mm, 170 mm, 160 mm, 150 mm, 140 mm, 130 mm, 120 mm, 110 mm, or 100 mm, in order to prevent injury to the larvae and to limit the size of the egg-growth chamber.

The angle of the surface onto which the larvae fall may be any angle that acts to separate multiple groups of larvae on contact. The angle of the surface may be at least 25°. Suitably, the angle is at least 30°, 35°, 40°, 45°, 50°, 55°, 60°, 65° or 70°. In embodiments, the angle of the surface is at most 80°, 75°, 70°, 65°, 60°, 55°, 50°, 45° or 40°.

Suitably, the angle of the surface may be in the range of from 30° to 80°. More suitably, the angle of the surface may be between 40° to 70°. In embodiments, the surface may be curved or formed of different angled sections such that the angle of the surface onto which the larvae fall varies between the above ranges depending on where on the surface contact is made. This allows optimisation of the drop height and angle of impact of all egg holders.

The combination of height and angle of the surface means that specific combinations are particularly suitable for separating the larvae. Suitably, the height of drop is in the range of 100 mm to 300 mm, suitably 150 mm for an angle of 70°; the height of drop is in the range of 300 mm to 400 mm, suitably 350 mm for an angle of 45°

When the larvae impact the surface it is important that they are not retained on, or stick to, the surface. Larvae remaining on the surface will require removal, by manual means or otherwise. Larvae stuck on the surface can die and decompose and/or can cause more larvae to stick. This can lead to reductions in efficiency and delays in production. In embodiments, the above angle/height combinations also mean that larvae are separated and then pass from the surface without sticking to, or remaining on, the surface.

In embodiments, the surface used for separating larvae into individuals according to this embodiment of the invention may be a flat surface, a curved surface or formed as part of a funnel to ensure the larvae are directed appropriately. The surface may be made of a suitable material to further reduce any occurrence of the larvae adhering to the surface, for example, the surface could be made from polished stainless steel or ultra-high-molecular-weight polyethylene (UHMWPE) with a polished natural surface. In addition, or instead, the surface may be coated with a non-stick coating such as PTFE, dry lubricant or hydrophobic spray.

In embodiments of the invention, the larvae passing from the separating surface are counted. Any means of counting the larvae is contemplated. Suitably, counting of the larvae is by physical means or by visual means. Suitably, the means of counting may be via breaking a light beam, such as an infra-red beam or laser, or alternatively through use of a charge detector. Alternatively or additionally, the mass of larvae passing from the surface can be determined. More suitably, counting is by automated visual means comprising a camera or other optical visualisation device and appropriate software to recognise and incrementally count or tally the number of larvae passing through its field of vision. Suitable systems for use in embodiments of the invention may comprise lasers, sensors other than cameras and capacitance-based sensor. Suitably, the larvae are caused to drop in front a camera that counts individuals as they pass. In embodiments, the camera may be a high frequency line scan camera or a high frequency area scan camera. Suitably, there may be provided a screen positioned opposite to the camera and behind the larvae to enhance or standardise visualisation. In embodiments, the screen may be any colour that allows the larvae to be visualised. Suitably the screen is maintained as a black or white colour. Suitably, when the screen is white, or any other light colour, the screen may be backlit to enhance visualisation. In embodiments where the screen is dark or black, the screen may have a matt finish and/or approximate to a black body. In one embodiment, the background screen is matt black and the larvae may be lit with a white foreground light to provide a contrast with the black background. A black screen may be preferred as the larvae are translucent and may permit transmission of white light through which may reduce the ability of the visualisation equipment to distinguish the larvae from the background. Larvae generally appear white on a black background.

Once a designated number of larvae, or a number of larvae within a designated range, has been counted, the container or surface comprising a food source to which the larvae are directed can be moved to ensure even distribution of larvae in the food source, or can be changed so that the larvae are then added to a new or different container. If the amount of food source in the container, or on the surface, is also controlled, then in this way the number of larvae in a given amount of food source can be controlled and optimised.

In embodiments, the egg-growth chamber comprises all of the one or more egg holders, the surface for separating the larvae into individuals, and the automated counting means. For superior efficiency, scale or spatial requirements the individual components may be spatially separated and the larvae transferred manually or mechanically, for example by use of conveyor belt, therebetween.

In an embodiment of the egg-growth chamber of the present invention, at least one of the egg holders is provided directly above the separation surface such that as the larvae pass from the egg holder they drop on the surface and are separated. In embodiments, more than one of the egg holders is positioned above the separation surface. Suitably, all of the egg holders present are positioned over the separation surface. Alternatively, the egg holders may be moveable such that they can move to a position above the separation surface either by manual or automated means. Suitably, the separation surface directs the larvae after impact such that the larvae drop in front of the visual counting system into a container comprising a specific quantity of food source. In this way, collection of a specific number, or range of number of larvae can be collected in a container comprising a specific quantity of food source. Suitably, the food source is of a composition, quality and moisture content suitable for optimised larval growth. Suitably, the food source is brewer's grains, coffee grains, vegetable matter or combinations thereof Turning now to the second stage of the process, the larvae in a food source are transferred to a larval chamber.

The larval chamber may be the container in which the larvae in the food source is contained. Alternatively, the larval chamber may comprises one or more repositories for larvae provided with a food source from the egg-growth chamber. In embodiments, the repository may be an inlet for accepting a conveyor on which the larvae in a food source is provided. This embodiment would also require a suitable outlet for the conveyor. The speed and/or length of the conveyor within the larval chamber can be adjusted to ensure that the residency time of the larvae within the larval chamber is sufficient, optionally as determined by the expected larval growth time based on an identified bell-curve distribution. More suitably, the one or more repositories are configured to accept a corresponding number of containers comprising larvae and a food source from the egg-growth chamber. In embodiments where the containers are in a suitable form, such as a tray or crate, then the one or more repositories may be in the form of drawers, racks or shelves. The number of repositories in the larval chamber is not limited and may be chosen to accommodate the expected number of containers to be received from the egg-growth chamber.

In embodiments, the larval chamber may accept larvae in a food source from one, or more than one egg-growth chamber(s).

In the larval chamber, environmental conditions are controlled to optimise growth and speed of growth of the larvae. The temperature is generally maintained in the larval chamber to be above 20° C. More suitably the temperature is generally maintained in the larval chamber to be above 25° C. Suitably the temperature within the larval chamber is above 21° C., 22° C., 23° C., 24° C., 25° C., 26° C., 27° C. or 28° C. The temperature is generally maintained in the larval chamber to be below 40° C. More suitably the temperature is generally maintained in the larval chamber to be below 35° C. Suitably the temperature within the larval chamber is no more than 29° C., 30° C., 31° C., 32° C., 33° C., 34° C., 35° C., 36° C., 37° C., 38° C., 39° C. or 40° C. Suitably the temperature is within the range of from 23° C. to 35° C. Suitably, the temperature is within the range of from 25° C. to 32° C. More suitably, the temperature is within the range of from 26° C. to 30° C. The humidity within the larval cage is carefully controlled, and generally held around 70% relative humidity (RH) as measured by a psychrometer or a hygrometer. Suitably the relative humidity in the larval chamber is at least 50%. Suitably the relative humidity is above 65%. The relative humidity may be above 66%, 67%, 68%, 69%, 70%, 71%, 72%, 73%, 74% or 75%. The relative humidity may be at most 80%. The relative humidity may be at most 79%, 78%, 77%, 76%, 75%, 74%, 73%, 72%, 71%. 70%, 69%, 68%, 67%, 66% or 65%. Suitably the relative humidity may be in the range from 60% to 80%. More suitably the relative humidity may be in the range of from 65% to 75%.

It is preferable to avoid build-up of condensation as this can lead to mould growth, poor larval health, and rusting of metal parts. In embodiments a constant air flow is maintained through the cage. Suitably, this can be provided for all parts of the larval chamber by a central fan or by a smaller, local, fans incorporated into, or associated with, parts of the larval chamber to provide fine tuning of the conditions.

Lighting conditions within the larval chamber should be controlled to promote healthy growth. Larvae feed on top of and within a food source when in a dark environment, however, in light conditions, the larvae move away from the light to within the food source. As environmental conditions are more difficult to control within the food source, in some embodiments the larva are placed in low-light or dark conditions in the larval chamber to allow then to feed in accordance with the natural tendencies.

It is important to keep the food source moist when in the larval chamber to enhance and optimise larval growth. Suitably the food source in the larval chamber should have a moisture content of at least 60% as measured by comparative weight of a sample before and after oven drying to constant weight. The moisture content can be at least 65%, 70%, or 75%. Suitably, the moisture content of the food source is at most 80%. The moisture content of the food source in the larval chamber is preferably in the range of 60% to 80%, more suitable from 65% to 75%. The food source is typically provided to the larvae with a moisture content within the desired range. The larval chamber or the repositories in the larval chamber are then configured to control moisture content. In embodiments, such configurations may comprise close fitment of the containers to the repository surroundings or alternatively, the humidity is maintained at a high level to limit evaporation. In embodiments, the containers may be sealed or partially sealed to control the moisture content of the food source. Alternatively, additional food may be added with a moisture content that compensates for any loss of moisture from the food already present. Additional food may be provided to the larvae in the larval chamber should it become necessary.

In an embodiment, after a predetermined time period, or when it is deemed that the larvae in a particular container in the larval chamber has reached a particular point on the posited bell-curve for development into pre-pupae the container holding the these larvae is removed from one end. A new container holding younger larvae and a food source may then be added at the other end. This arrangement is sometimes referred to as a 'First In First Out' (FIFO) methodology in materials handling systems.

In order to aid the growth process, conditions for the larvae are preferably aerobic. The process needs to ensure that any larvae underneath the food source or larvae on the surface of the food source are also kept in the same conditions. In embodiments, therefore, an agitation means may be included which from time to time moves the larvae or the food source containing the larvae so giving a greater chance so that each larva will be subject to the same conditions overall. Examples of suitable agitation systems are mechanical stirring apparatus, miniature plough systems, vibration, flipping of the container, or partial flipping of the container.

Once the larvae have grown to a sufficient size, and develop into pre-pupae, the exoskeletons of the larvae start to harden, and darken. It is of advantage at this stage to assist the pre-pupae in drying. One option is to include a ramp which the pre-pupae are able to crawl up, and which ties in with the instinct of pre-pupae to move upwards to find a suitable place to pupate. Optionally at this stage, air can be drawn over the pre-pupae to assist in the drying process. The air being drawn over the pre-pupae can be heated to aid the drying process, preferably to a temperature of from 23° C. to 35° C.

Once the pre-pupae have so migrated they can be removed manually. In this embodiment, once the pre-pupae have been removed they are placed onto a sleeping medium, within the third stage of the process of the present invention, the pupation chamber. The pupation chamber acts to optimise conditions for the pupal stage from which the adult fly will eventually emerge. The sleeping medium may be a dry substrate forming a layer in an enclosed area such as a tray.

Providing a relatively dry environment (i.e. a relative humidity less than that of the larval chamber) acts to dry out the pre-pupae to induce sleep and metamorphosis. The substrate can be any suitable material. Suitably the substrate is selected from the group consisting of plastic spheres; sawdust; zeolites; and/or dried food source, optionally recycled from other stages of the breeding process and introduced in reduced amount having been dried separately from the larvae. Care should be taken when selecting the materials (particularly in the case of sawdust which may have come from a treated wood source) that those do not include materials harmful to the pupae. Additionally, the substrate material is suitably formed from particles of smaller size then the pupae as this enables a sieving process to be used to separate the pupae from substrate at a later stage. Again, conditions within the pupation cage are controlled to those which optimise conditions for the pupa or which optimise, subject to commercial constraints such as energy usage.

After a predetermined time period, for example one week, the pupae are passed through a system to separate larvae, or pre-pupae which are awake from the pupae which are asleep.

In one embodiment, the separation method involves a system of sieves. For example, in a passive sieving system, the pupae are passed onto a coarse sieve comprising one or more layers, suitably two layers, which initially catches the pupae and allows the substrate material through. In embodiments, a light source shining on the coarse sieve(s) acts to cause larvae or pre-pupae that are present which are awake to crawl away from the light. The positioning of the light source is such that the larvae or pre-pupae are thus directed from the coarse sieve(s) onto a finer sieve. The mesh of the finer sieve is such that larvae or pre-pupae are retained but the substrate passes through.

The substrate, pupae and awake larvae and pre-pupae are thus separated. The substrate can either be safely disposed of or treated for reuse. The awake larvae may be returned to the larval chamber or disposed of.

The pupae are placed onto trays which are then transferred to the pupation chamber.

Alternatively, it has been surprisingly found that there is no need to rely on self-migration of the pre-pupae to separate the pre-pupae from the food source prior to transfer to the pupation chamber.

In an embodiment, drying of the food source in which the pre-pupae are present in the pupation chamber is sufficient to result in good levels and rates of pupae formation. This approach has numerous advantages over the prior art methods of pre-pupal migration. Firstly, it means that the same containers, or surface can be used from collection in the egg-growth chamber through to leaving the pupation chamber. It also obviates the need for a ramp and separate apparatus for the pre-pupae to ascend. It also means that the process is no longer reliant on the pre-pupae self-selecting for pupation which can be subject to significant variation and dependent on environmental conditions. The simplicity of the approach makes it ideal for scaling of the process for commercial purposes.

Environmental conditions in the pupation chamber for drying of the separated pupae or drying of the food source containing the pupae is substantially similar. It is therefore possible to combine pupae from different sources either isolated from the food source or within it in the same pupation chamber, In embodiments, drying of the food source in which the pupae are present in may be encouraged by allowing a greater headspace above each container to enhance airflow and resultant evaporation. Additional drying may be obtained by having a temperature and relative humidity in the pupation chamber that encourages evaporation of moisture and/or increasing the air flow over the food source.

Suitably the target moisture content of the food source in the pupation chamber should be less than 60%. The moisture content should be less than 55%, 50%, 45% or 40%. The moisture content of the food source in the larval chamber is preferably in the range of 0% to 60%, more suitably from 20% to 60%.

In the pupation chamber, environmental conditions are controlled to optimise pupation. The temperature is generally maintained in the pupation chamber to be above 20° C. More suitably the temperature is generally maintained in the larval chamber to be above 25° C. Suitably the temperature within the larval chamber is above 21° C., 22° C., 23° C., 24° C., 25° C., 26° C., 27° C. or 28° C. The temperature is generally maintained in the larval chamber to be below 40° C. More suitably the temperature is generally maintained in the larval chamber to be below 35° C.

Suitably the temperature within the larval chamber is no more than 29° C., 30° C., 31° C., 32° C., 33° C., 34° C., 35° C., 36° C., 37° C., 38° C., 39° C. or 40° C. Suitably the temperature is within the range of from 23° C. to 35° C. Suitably, the temperature is within the range of from 25° C. to 32° C. More suitably, the temperature is within the range of from 26° C. to 30° C.

The humidity within the pupation chamber is carefully controlled, and generally less than the relative humidity of the larval chamber. The relative humidity in the pupation chamber is generally held below 60% relative humidity (RH) as measured by a psychrometer or a hygrometer. Suitably the relative humidity in the pupation chamber is at least 10%. Suitably the relative humidity is above 20%. The relative humidity may be above 25%, 30%, 35%, 40%, 50%, or 55%. The relative humidity may be a most 60%. The relative humidity may be at most 55%, 50%, 45%, 40%, 35% or 30%. Suitably the relative humidity may be in the range from 10% to 70%. More suitably the relative humidity may be in the range of from 20% to 60%.

Pre-pupae and/or pupae generally prefer dark conditions therefore the pupation chamber is suitably maintained in low-light or dark conditions.

In line with the natural variation of individual lifecycles, and the fact that it is envisaged that in some embodiments, eggs/larvae of different ages will be combined into single batches for the process, some pupae will emerge as adult flies in the pupation chamber. In some embodiments, a lid is therefore added over the containers or the surface on which the pupae are present to prevent escape. In embodiments where the lid is on a container, such as a tray or crate, the lid adds additional height to the container to accommodate the additional headspace requirements of the adult flies in the container. Suitably the lid has openings, optionally a mesh or netting that continues to allow good air circulation and does not inhibit drying. Suitably the mesh or netting has openings smaller than that of an adult fly to prevent escape or loss of flies from the container.

In some embodiments the lid also incorporates an opening that is operable between an open and closed position that prevents escape of flies when the container and lid is in the pupation chamber yet allows the adult flies to leave the container and lid when in the release box.

The container with lid containing the food source and the pre-pupae developing into pupae may be considered the larval chamber in accordance with the present invention.

In alternative embodiments, the pupation chamber comprises one or more repositories for pre-pupae, either provided with a food source or not, from the larval chamber. In embodiments, the repository may be an inlet for accepting a conveyor on which the pre-pupae in a food source is provided. This embodiment would also require a suitable outlet for the conveyor. The speed and/or length of the conveyor within the pupation chamber can be adjusted to ensure that the residency time of the pre-pupae and the pupae developed therefrom within the pupation chamber is sufficient, optionally as determined by the expected pupation time based on an identified bell-curve distribution. More suitably, the one or more repositories are configured to accept a corresponding number of containers comprising pre-pupae, with a food source or not, from the larval chamber, In embodiments where the containers are in a suitable form, such as a tray or crate, then the one or more repositories may be in the form of drawers, racks or shelves. The number of repositories in the pupation chamber is not limited and may be chosen to accommodate the expected number of containers to be received from the larval chamber.

Once a suitable time has passed and it is anticipated, based on the bell-shaped curve of pupation of the pupae in the pupation chamber, that the late-stage pupae have begun to or are about to emerge as adult flies, the pupae are transferred from the pupation chamber to the release box.

The environment in the release box is controlled to optimise the final stages of metamorphosis of the pupae into adult flies. The temperature is generally maintained in the release box to be above 20° C. More suitably the temperature is generally maintained in the release box to be above 25° C. Suitably the temperature within the release box is above 21° C., 22° C., 23° C., 24° C., 25° C., 26° C., 27° C. or 28° C. The temperature is generally maintained in the release box to be below 40° C. More suitably the temperature is generally maintained in the release box to be below 35° C. Suitably the temperature within the release box is no more than 29° C., 30° C., 31° C., 32° C., 33° C., 34° C., 35° C., 36° C., 37° C., 38° C., 39° C. or 40° C. Suitably the temperature is within the range of from 23° C. to 35° C. Suitably, the temperature is within the range of from 25° C. to 32° C. More suitably, the temperature is within the range of from 26° C. to 30° C.

The humidity within the release box is carefully controlled. The relative humidity in the release box is generally held below 60% relative humidity (RH) as measured by a psychrometer or a hygrometer. Suitably the relative humidity in the release box is at least 10%. Suitably the relative humidity is above 20%. The relative humidity may be above 25%, 30%, 35%, 40%, 50%, or 55%. The relative humidity may be a most 60%. The relative humidity may be at most 55%, 50%, 45%, 40%, 35% or 30%. Suitably the relative humidity may be in the range from 10% to 70%. More suitably the relative humidity may be in the range of from 20% to 60%.

As pupae prefer dark conditions, the release box is maintained in low light or in the dark.

Maintaining low light or dark conditions in the release box also has the advantage of encouraging the emergent adult flies in accordance with their natural behaviour to seek light to leave the release box in to the relative light conditions of the breeding chamber.

In embodiments, the container and lid containing the pupae and the adult flies and the food source is the release box in accordance with the present invention.

In alternative embodiments, the release box comprises one or more discrete positions or repositories for pupae, either provided with a food source or not, from the pupation chamber. In embodiments, the repository may be an inlet for accepting a conveyor on which the pupae in a food source or separated from the food source is provided. This embodiment would also require a suitable outlet for the conveyor. More suitably, the one or more repositories are configured to accept a corresponding number of containers comprising pupae, with a food source or not, from the pupation chamber, In embodiments where the containers are in a suitable form, such as a tray or crate, then the one or more repositories may be in the form of drawers, racks or shelves. The number of repositories in the pupation chamber is not limited and may be chosen to accommodate the expected number of containers to be received from the pupation chamber.

Such an arrangement aids in the maintenance of a constant flow of new pupae, and allows for pupae at different stages to be held together to provide a relatively constant production of adult insects. The walls of the release boxes can be formed of a plastics material, or alternatively from a metal. Preferably, the walls are made of food grade materials to minimise the risk of harm to the insects.

In an embodiment, the release box has one or more outlets for the release of the emergent adult flies into the breeding chamber. Suitably, the number of and size of the outlets may be varied depending on the number of pupae, and hence the number of expected flies that will emerge from the pupae. The size and number of outlets may also be varied depending on the need to allow light and chemical attracts through into the release chamber to encourage flies to travel from the release box to the breeding chamber. The number of outlets for a release box designed to accommodate 30,000 pupae at a given time would suitably have 6 outlets, wherein the outlets have a total surface area of 300 $cm^2$ (approximately 6×50 $cm^2$ although there is no requirements for the outlets to be the same size as one another).

In embodiments, the area of the outlets per pupa in the release box may be at least 0.005 $cm^2$/pupa. Suitably, the area of the outlets per pupa in the release box may be at least 0.006 $cm^2$/pupa, 0.007 $cm^2$/pupa, 0.008 $cm^2$/pupa, 0.009 $cm^2$/pupa or 0.010 $cm^2$/pupa. The area of the outlets per pupa in the release box may be less than 0.050 $cm^2$/pupa. Suitably, the area of the outlets per pupa in the release box may be less than 0.040 $cm^2$/pupa, 0.030 $cm^2$/pupa, 0.020 $cm^2$/pupa, 0.009 $cm^2$/pupa or 0.010 $cm^2$/pupa. Suitably, the area of the outlets per pupa in the release box may be in the range of from 0.001 $cm^2$/pupa to 0.05 $cm^2$/pupa. More suitably, the area of the outlets per pupa in the release box may be in the range of from 0.005 $cm^2$/pupa to 0.030 $cm^2$/pupa. The release box may also be fitted with mechanical means to encourage flies to exit to a breeding chamber. One such means is a fan or blower that pushes air from the release box to the breeding chamber via the one or more outlets. Alternatively, an eccentrically weighted spinning shaft creating a vibration in the release box could be used.

The outlets of the release box may be of any suitable shape. Suitably the outlets are square, circular or rectangular in cross-section. The outlets may be alignable with corresponding inlets to the breading chamber or one or more inlets may open on to an open side of the breeding chamber which is sealed to the release box. The outlets may align with one or more breeding chambers sequentially or simultaneously.

In an embodiment, the or each outlet from the release box may be fitted with a means for counting the flies that pass therethrough. Counting of flies entering the breeding chamber from the release box means that the number of flies in a given breeding chamber at one time can be controlled for optimal conditions. In an embodiment, the means of counting flies passing through the outlet may be in the form of a proximity sensor such as breaking a light beam, passive infra-red system. Other methods of counting the flies in or emerging from the release box include using an area scan camera with a viewing plane created by transparent sheets making letterbox shapes for the flies to crawl through. Another method is taking images of the flies within the breeding chamber to work out from the population density on the walls of the chamber if it is full. In embodiments, the outlet comprises a grid or mesh or net or other form of sectioning to provide channels in each outlet which can be suitably monitored for the passage of flies. Suitably the holes or apertures may be in the range of 6 mm to 14 mm. More suitably the holes or apertures may be in the range from 9 mm to 11 mm. The flies may be made to stop to crawl through the openings making it easier for the system to count the individuals. The number of holes or apertures may be varied to optimise fly transfer through the outlet. Suitably the diameter of each outlet is between 80 mm and 120 mm. More suitably the outlet has a diameter of 100 mm. Suitably, the outlet comprises a grid wherein each opening in the grid is sized to allow the passage of a single fly at once.

Alternatively, each opening in the or each outlet may be fitted with a means of detecting the passage of a fly.

In embodiments, the outlets of the release box may be fitted with some means of preventing return of flies to the release box from the breeding chamber. Any suitable means of preventing return of the flies is contemplated including narrowing of the channels in the outlets or some form of flap or cover.

The means of counting flies can be, for example, an infra-red system in which breaking a beam of infrared radiation registers as an individual fly leaving the box Additionally, or alternatively the sensor can include a camera to enable a visual check to be carried out. The system can be set up such that once a pre-set number of flies have emerged, the exit is shut and a neighbouring box opened. Operation of the gate may be manual or mediated by a solenoid or other part of a gate opening and closure mechanism. Additionally, a notification can be sent to a user or to a processor to pass on the information that the required number of adults has emerged.

Counting of emerging flies may also provide a useful indication of how many pupae remain in the release box. This can be used to cause the operation such that the release box is removed and replaced by a fresh release box and/or container. This operation can be either carried out manually or via automated means.

After a further time has elapsed, the box is once again opened to allow further flies to be released from that box. The rate of collection of flies can thus be determined and therefore the rate of production of eggs back into the cycle.

The release box may be associated with one breeding chamber. In embodiments, to further enhance the scalability of the apparatus, the or each release box may be associated with two or more breeding chambers and the release box may be moved between each breeding chamber to release flies therein as required. This enables the release box to move to a new breeding chamber to constantly fill the breeding chambers, and also to allow switching of breeding chambers to maintain continuous production when one breeding chamber needs to be taken offline for emptying and cleaning.

The release box may have means for it to be moved between the one or more breeding chambers. Alternatively, the breeding chambers may be moveable to engage with one or more release boxes. Suitably, the release box may be mounted on a moving track or on a turntable in order for one set of outlets to engage with a number of breeding chambers.

In embodiments where the pupae are provided to the release chamber in containers, once the majority of adults are deemed to have emerged from a given container, then the container can be removed and replaced with a container holding a new batch. Optionally pupae that are yet to emerge as adult flies can be returned to a container.

To optimise efficient use of heating, containers maybe arranged next to each other in a release box. Again, based on the statistical distribution of the likelihood of emergence of the adult, corresponding to a bell-curve, the optimum time for collection and maintenance of a container can be determined following expiry of the pre-set time, the release box is removed for cleaning, and replaced with a new container containing a new batch of pupae. The container formerly present is cleaned for re-use or disposed of.

Turning now to the fifth stage of the apparatus of the present invention, the breeding chamber. Adult flies which have emerged and left a release box enter a breeding chamber and are allowed to mate to ensure that the next generation of eggs can be produced. The breeding chamber may take the form of any simple enclosure. In embodiments, the breeding chamber is formed of a fabric or mesh enclosure or tent or similar to allow light and air to enter the chamber, and for the chamber to be easily cleaned. Breeding chambers formed of other materials such as metal or plastic are alternatives.

In the breeding chamber the light is adjusted and utilised as a trigger for mating. For example, the flies are subjected to light for a certain number of minutes per day, and in a pre-determined pattern. An unnatural lighting pattern has been found to be effective. Additionally, pheromones or other chemical stimulants can be released into the mating box to stimulate mating. Typically, an adult will remain in the breeding chamber for up to 7 days. As in nature, once the adult male fly has mated, it dies. The females tend to die after mating and laying their eggs.

Female black soldier flies (FBSF) prefer to lay eggs in crevices and further preferably above or near to, or adjacent to a food source. BSFs are therefore distinguished from the common house fly which prefers to lay eggs directly onto the food source. Although the size of an egg, and thus the size of the crevice sought by the female varies, the crevices are typically 0.5 to 5 mm in size. The size is a function of the size of the female. Moreover, larger females tend to lay more eggs and so provision is optionally made to determine the average size of the females within a batch and thus provide more laying sites of a suitable size.

One option is to provide a plurality of ovipositing racks. The ovipositing racks can be in the form of a slit, crevice or hole, sized for the female to be able to insert her ovipositor. Traps can be provided in the form of hollow tubes or straws which are set into an arrangement which maximises provision of the egg-laying volume, in one embodiment being similar to the layout of cells in a honeycomb. The female can then lay eggs within the straw's body. Alternatively, one or more corrugated cardboard sheets can be used. In a further alternative, a stack of strips formed of a suitable material provides suitable ovipositing positions in the gaps between the strips. The strips may be formed of any suitable material, for example wood, plastic, metal or a hybrid materials between plastic and natural material. It is believed that FBSFs prefer to lay eggs on wooden structures, presumably due to the similarity to natural egg-laying sites. The shape of the opening of the crevices may be hexagonal, other shapes such as square, circular or elongated channels can also be used in a suitable packing arrangement of adjacent crevices can be devised. Typically, a crevice having a width 0.5-5 mm is suitable.

Artificial means to attract the FBSF to the ovipositing rack may be used. To assist in enticing the FBSF to lay eggs in the desired location, the crevices may be located above a source of food, optionally in a tray having low side-walls relative to the base area of the container. Additionally or alternatively, an attractant other than a food source can be included to encourage the FBSF to lay eggs where desired. Examples of other attractants include fertilised eggs, decaying material and deceased larvae, pre-pupae and pupae. In an embodiment, an air flow can be created from the food or chemical attractant to the ovipositing rack. The air flow may be created using, for example, a conventional fan.

Monitoring may be undertaken to determine the number of eggs laid within a particular egg-ovipositing rack. Monitoring may be via direct observation by an operative of the ovipositing racks, or can be carried out remotely. An example of remote monitoring may be via an imaging system that can be used to enable inspection to be carried out remotely. Additionally, or alternatively a camera or other imaging system can be utilised to determine when a position on an ovipositing rack is filled, by measurement of the light transmission through that position. For example, in the example where the ovipositing rack comprises a plurality of straws, a light source is positioned at one end of a straw with detectors at the other end of the straw: a processor determining when the light blocked is consistent with an egg being present. Alternatively, an automatic egg-counting system can be installed. One particularly suitable method removes the ovipositing rack on a time schedule as the age, or spread of age, of the eggs is more important than efficiency or completeness of fill.

In order to facilitate the overall process of egg gathering from the ovipositing rack, the ovipositing racks may be housed within a removable appendage to the breeding chamber, the removable appendage is so mounted to be moveable between different locations without disturbing the eggs contained therein. Once it is determined therefore that an ovipositing rack contains sufficient eggs or optionally additionally the growing larvae within the eggs are ready to hatch, the removable appendage comprising the ovipositing rack is removed and replaced with a new ovipositing rack in the same or a new removable appendage. The fertilised eggs are then removed from the removed ovipositing rack and placed in an egg holder in the egg-growth chamber. In embodiments, the amount or number or fertilised eggs may be determined by weighing the eggs, either by putting them on a tared substrate, or by having the hatchling tray/egg holder weight sufficiently little that it can be weighed with the eggs to a sufficiently high precision. As in some embodiments, most of the above process takes place in the same individual tray or compartment, each of which carries a population of insects close together in the life cycle, the apparatus to carry out the method can be modular, which allows for scalability.

In an embodiment, the ovipositing rack may be used as an egg holder in the egg growth chamber. Suitably, the ovipositing rack may be removed from the breeding chamber and placed in the egg-growth chamber. Alternatively, the breeding chamber and the egg-growth chamber may be linked or occupy the same internal space such that gravid females may lay their eggs in the ovipositing rack which may then act as an egg holder to provide a position for the eggs to mature and hatch as larvae from which they pass to the food source.

Additionally, data on humidity, temperature etc. can be gathered. Processing can be carried out via machine learning algorithms which enable improved monitoring to take place.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed processes and compositions, the exemplary processes, devices and materials are described herein. It is to be understood that this disclosure is not limited to particular methods, and experimental conditions described, as such processes and conditions may vary.

Example 1—Larvae Separation

A sheet of steel was placed under egg holders formed of a mesh material; the mesh having a hole size of 2 mm$^2$. The angle of the sheet was varied and the number of larvae present on the steel sheet and the area on which larvae dropped after contact with the steel sheet were recorded over a one minute period. The distance from drop point to sheet of steel varied between 130 mm and 350 mm as the sheet was angled below a number of egg holders.

Figure 2:
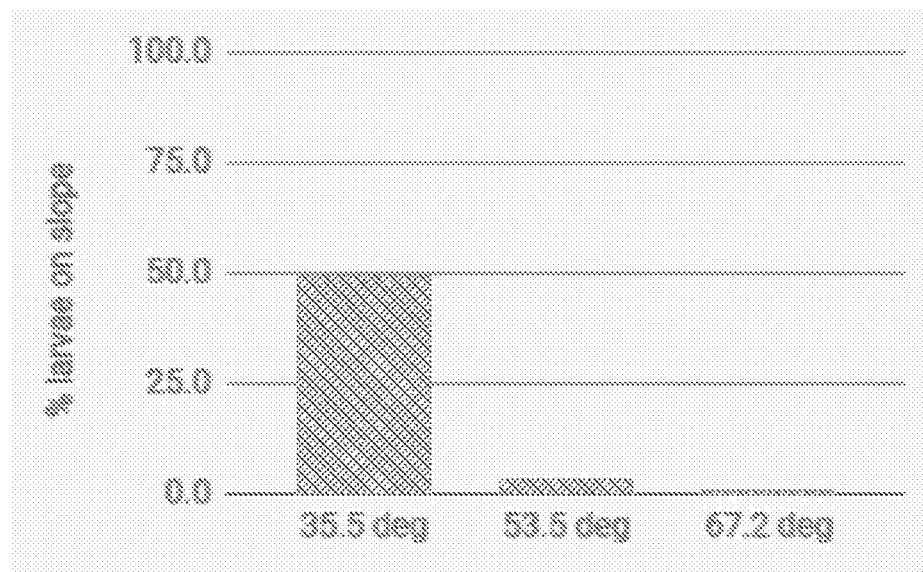
FIG. 2 shows the % larvae remaining on a slope at varying angles after being dropped from a given height.

Results
Larvae Falling Profile
Fall quantity of larvae falling in groups of greater than one=4 (26.7%)
Fall quantity of larvae falling as individuals=11 (73.3%)
Larvae Landing Profile
Fall quantity of larvae falling in groups of greater than one=0 (0%)
Fall quantity of larvae falling as individuals=139 (100%)
Slope Effect
The effects of angle of the plate on which larvae fall is shown in FIG. 2.

The height of the larvae above the slope was also observed to have an effect with the majority of larvae remaining on the 35.5° angled slope, while the majority of the larvae did not remain on the slope when the angle was 53.5° or 67.2°.

Conclusions
The difference between the falling and landing multi and single larvae clearly shows that the impact on the slope is causing the larvae to separate.

The angle of the slope makes significant impact on the number of larvae that remain on it after impact.

Example 2—Height of Drop and Angle of Surface in Larvae Counter

Figure 3A:
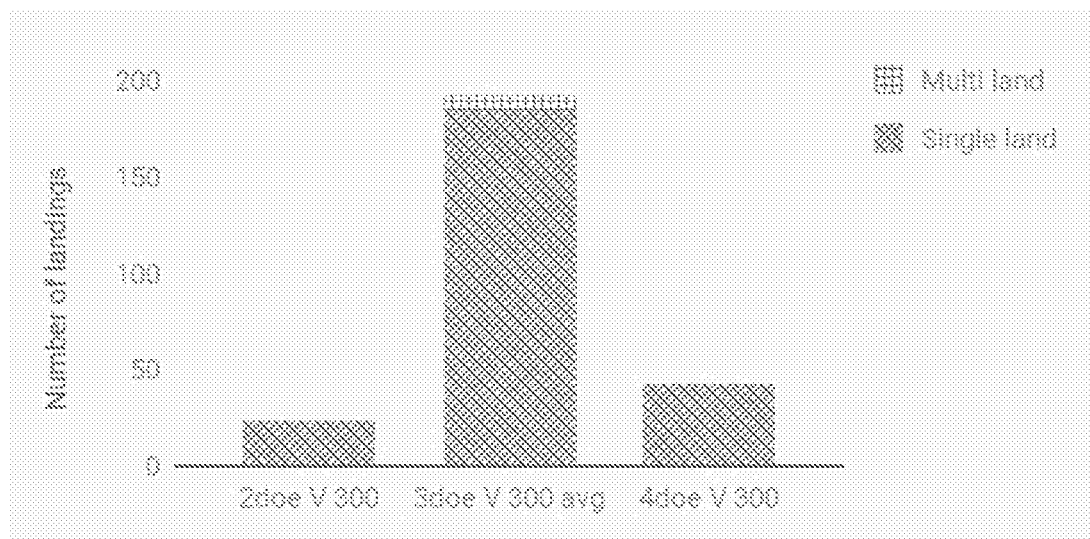
FIGS. 3a and 3b show the varying effect on multiple larvae drop from the egg holders by age and fall rate.
Figure 3B:
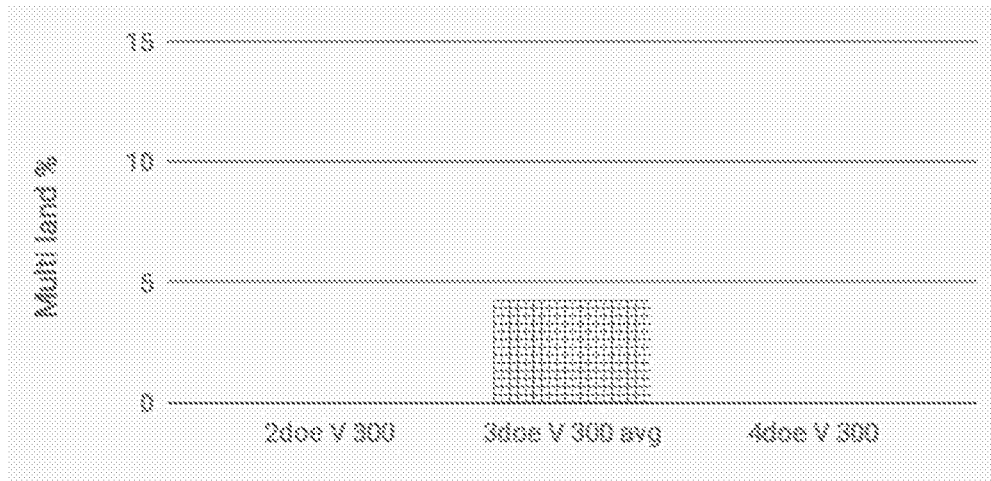
Figure 4A:
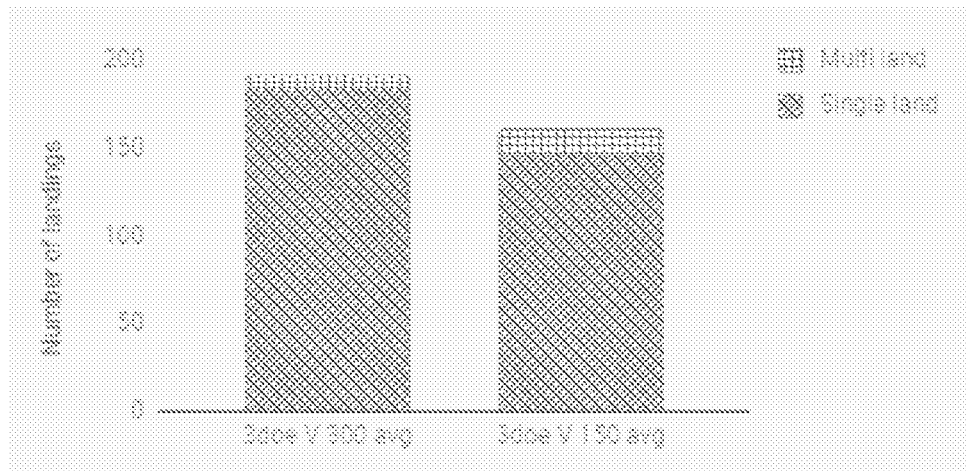
FIGS. 4a and 4b shows the varying effect on multiple larvae drop from the egg holders by drop height.
Figure 4B:
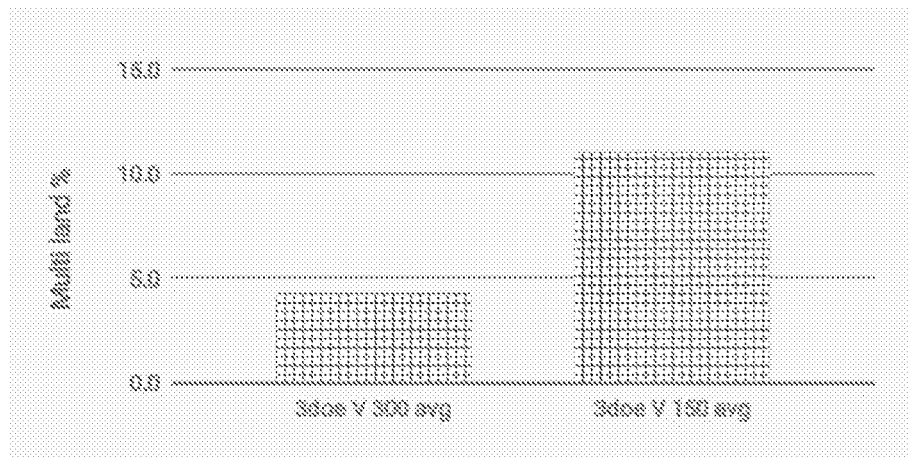
Figure 5A:
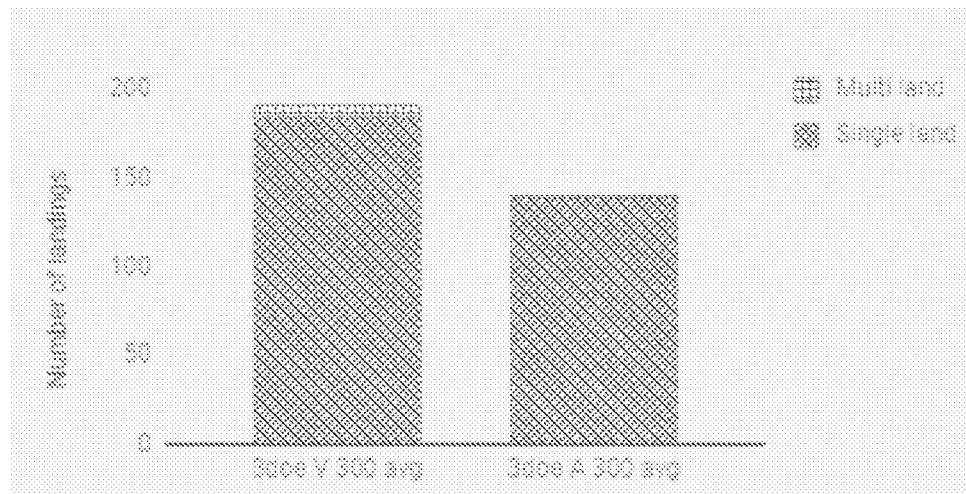
FIGS. 5a and 5b shows the varying effect on multiple larvae drop from the egg holders by angle of surface.
Figure 5B:
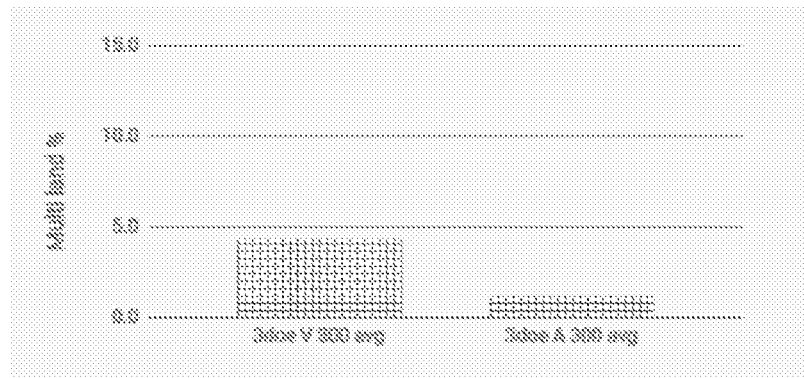

Two experiments were carried out to determine the landing characteristics of larvae dropping onto a surface,
Test 1 investigated the landing characteristics of larvae dropping vertically down onto a piece of black card at two different heights;
Test 2 bounced the larvae off an intermediary plate before reaching the black card.
Experimental Procedure
Test 1—Vertical Drop
Larvae from 2 day, 3 day and 4 day old eggs were dropped from two different heights, 300 mm and 150 mm and the horizontal landing position was monitored for at five minute intervals. Measurement of larvae landing singularly or in groups was then made.
Test 2—Angled Drop
Larvae from 2 day, 3 day and 4 day old eggs were dropped from 300 mm height, bounced off a plate angled at 66.4° to vertical. The same metrics as in test 1 were measured.
Key to Results Labelling:
2doe=2 day old eggs
3doe=3 day old eggs
4doe=4 day old eggs
V=Vertical
A=Angled
300=300 mm height drop
150=150 mm height drop
2=second test with same parameters (no value means first test with these parameters)
Larvae Multi Landing Vs Single Landing
The results have been separated into three sections to allow direct comparison between the key features that appear to affect the landing type.
FIGS. 3a and 3b: Larvae Multi Landing vs single landing—age of eggs/fall rate FIGS. 4a and 4b: Larvae Multi Landing vs single landing—fall height FIGS. 5a and 5b: Larvae Multi Landing vs single landing—Vertical vs Angled Conclusions Single Land Vs Multi Land Higher fall rates of larvae mean a greater density of larvae on the mesh falling which means they are more likely to fall in groups.

Falling from a greater vertical height increases the likely separation of the larvae once they hit the floor below them.

Hitting an angled plate reduces the number of multi landing as the initial bounce separates many of them.

Example 3—Drying of the Pre-Pupae in a Food Source

A container with lid, in accordance with the present invention, holding pre-pupae in a food source was placed in a pupation chamber in accordance with the present invention. The food source initially has a moisture content of 78.8% as measured by oven-drying the samples at 100° C. for 3-4 hours and measuring the weight before and after. The pupation chamber was maintained at 28° C.+/−2° C. and a relative humidity of 70% for 15 days. At the end of the drying period the food source had a moisture content of 58.8%, again measured by oven-drying the samples and measuring the weight before and after.

By visual inspection the majority of the pre-pupae had developed into pupae.

Although particular embodiments of the invention have been disclosed herein in detail, this has been done by way of example and for the purposes of illustration only. The aforementioned embodiments are not intended to be limiting with respect to the scope of the invention. It is contemplated by the inventors that various substitutions, alterations, and modifications may be made to the invention without departing from the spirit and scope of the invention.

Alternative expressions of the inventive concept are set out in the following clauses:

Clauses

1) A modular system for breeding flies, comprising:
an egg-growth chamber configured to receive fertilised eggs and to permit the fertilised eggs to develop and hatch as larvae, the egg-growth chamber comprising at least one egg holder, the or each egg holder being adapted to retain the fertilized eggs and allow passage of the larvae from the egg-holder to a food source to provide larvae in the food source;
a larval chamber configured to receive the larvae in the food source and to permit the larvae to feed on the food source and develop into pre-pupae to provide pre-pupae in the food source;
a pupation chamber configured to receive the pre-pupae in the food source and to permit the pre-pupae to develop into pupae, the pupation chamber being configured to dry the food source and the pre-pupae to provide pupae in a dried food source;
a release box configured to receive the pupae in the dried food source and to permit the pupae to develop into adult flies, the release box comprising one or more outlets for adult flies to leave the release box; and
a breeding chamber configured to receive adult flies via the one or more outlets in the release box and to permit adult flies to mate to provide gravid females, and wherein the gravid females oviposit fertilised eggs in one or more ovipositing racks.

2) The modular system of Clause 1, wherein one or more of the egg-growth chamber, larval chamber, pupation chamber, release box and breeding chamber has controlled environmental conditions.

3) The modular system of Clause 1 or Clause 2, wherein the egg-growth chamber is maintained at a relative humidity of from 60% to 80% and at a temperature in the range of from 25° C. to 32° C.

4) The modular system of any one of Clauses 1 to 3, wherein the larval chamber is maintained at a relative humidity of from 60% to 80% and at a temperature in the range of from 25° C. to 32° C.

5) The modular system of any one of Clauses 1 to 4, wherein the pupation chamber is maintained at a relative humidity of 20% to 60% and at a temperature in the range from 25° C. to 32° C.

6) The modular system of any one of Clauses 1 to 5, wherein the release box is maintained at a relative humidity of from 20% to 60% and at a temperature in the range of from 25° C. to 32° C.

7) The modular system of any one of Clauses 1 to 6, wherein the breeding chamber is maintained at a relative humidity of from 60% to 80% and at a temperature in the range of from 25° C. to 32° C.

8) The modular system of any one of Clauses 1 to 7, wherein the at least one egg holder in the egg-growth chamber is positioned to permit the larvae to drop from the at least one egg holder into the food source.

9) The modular system of any one of Clauses 1 to 8, wherein the at least one egg holder has one or more perforations sized to retain fertilised eggs and allow larvae to pass through.

10) The modular system of Clause 9, wherein the one or more perforations have a diameter in the range of from 0.5 mm to 3 mm.

11) The modular system of any one of Clauses 1 to 10, wherein the larval chamber, the pupation chamber and/or the release box is a container.

12) The modular system of Clause 11, wherein the larval chamber, the pupation chamber and/or the release box are the same container.

13) The modular system of Clause 11 or Clause 12, wherein the pupation chamber and/or the release box further comprises a lid that covers the container.

14) The modular system of Clause 13, wherein the lid comprises the one or more outlets.

15) The modular system of any one of Clauses 1 to 10, wherein the larval chamber has one or more discrete positions for receiving separate batches of larvae in the food source.

16) The modular system of Clause 15 wherein the one or more discrete positions are selected from the group consisting of: shelves; racks; and drawers.

17) The modular system of Clause 15 or Clause 16, wherein the larvae in the food source are within a container that is dimensioned to be placed in one of the one or more discrete position in the larval chamber.

18) The modular system of any one of Clauses 1 to 17, wherein the pupation chamber has one or more discrete positions for receiving different batches of pre-pupae in the food source.

19) The modular system of Clause 18, wherein the one or more discrete positions are selected from the group consisting of: shelves; racks; and drawers.

20) The modular system of any one of Clauses 17 to 19, wherein the pre-pupae in the food source are within a container with a lid, wherein the lid covers the container, and wherein the container with lid is dimensioned to be placed in one of the one or more discrete positions in the pupation chamber.

21) The modular system of Clause 20, wherein the lid has perforations for ventilation, the perforations sized to prevent the adult flies leaving the container.

22) The modular system of Clause 20 or Clause 21, wherein the lid has at least one opening which is operable between an open and a closed position, the opening being in a closed position in the pupation chamber.

23) The modular system of any one of Clauses 1 to 22, wherein light is at least partially excluded from the pupation chamber.

24) The modular system of any one of Clauses 1 to 23, wherein the release box has one or more discrete positions for receiving different batches of pupae in the food source.

25) The modular system of Clause 24, wherein the one or more discrete positions are selected from the group consisting of: shelves; racks; and drawers.

26) The modular system of Clause 24 or Clause 25, wherein the pre-pupae in the food source are within a container with a lid, the container and lid dimensioned to be placed in one of the one or more discrete positions in the release box.

27) The modular system of Clause 26 wherein the lid has perforations for ventilation sized to prevent the adult flies leaving the container.

28) The modular system of Clause 26 or Clause 27, wherein the lid has an opening which is operable between an open and closed position, the opening being in an open position in the release box.

29) The modular system of any one of Clauses 17 to 28, wherein the same container is used to sequentially pass from the larval chamber, to the pupation chamber to the release box.

30) The modular system of any one of Clauses 20 to 29, wherein the same lid is used on the same container from the pupation chamber to the release box.

31) The modular system of any one of Clauses 1 to 30, wherein the system comprises one or more of each of the egg-growth chambers, larval chambers, pupation chambers, release boxes and breeding chambers to accommodate the different lengths of time required in the lifecycle of the fly for each stage.

32) The modular system of any one of Clauses 15 to 31, wherein the system comprises differing numbers of discrete positions in each of the larval chambers, pupation chambers and release boxes to accommodate differing quantities of containers at each stage.

33) The modular system of any one of Clauses 1 to 32, wherein the food source prior to the pupation chamber has a moisture content in the range of from 60% to 80%.

34) The modular system of any one of Clauses 1 to 33, wherein the food source after drying in the pupation chamber has a moisture content of less than 60%.

35) The modular system of any one of Clauses 1 to 34, wherein the pupation chamber is maintained at a relative humidity of from 10% to 20% below that of the larval chamber.

36) The modular system of any one of Clauses 1 to 35, wherein the release box has between two and ten outlets.

37) The modular system of Clause 36, wherein the release box has six outlets.

38) The modular system of any one of Clauses 1 to 37, wherein the outlets in the release box have a total surface area in the range of from 0.005 $cm^2$ per pupa to 0.03 $cm^2$ per pupa.

39) The modular system of any one of Clauses 1 to 38, wherein the breeding chamber has lighting and/or chemical attractants to attract the adult flies from the release box to the breeding chamber.

40) The modular system of any one of Clauses 1 to 39, wherein the ovipositing racks have crevices, cracks or orifices in which the gravid females lay fertilised eggs.

41) The modular system of Clause 40, wherein the crevices, cracks or orifices have a diameter in the range of from 0.5 mm to 5 mm.

42) The modular system of Clause 40 or Clause 41, wherein the ovipositing racks are removable.

43) The modular system of any one of Clauses 1 to 42, wherein the egg growth chamber further comprises apparatus for counting larvae emerging from the fertilized eggs.

44) The modular system of any one of Clauses 1 to 43, wherein the apparatus for counting larvae emerging from fertilized eggs of a fly comprises one or more or all of the features of the system of Clauses 147 to 159.

45) The modular system of any one of Clauses 1 to 44, wherein the or each outlet on the release box comprises a counter which counts the number of adult flies leaving the release box wherein the breeding chamber is adapted to receive a specific number of adult flies from the one or more inlets of the release box.

46) The modular system of any one of Clauses 1 to 45, wherein the release box comprises one or more or all of the features of the release box of Clauses 162 to 176.

47) A process for breeding flies, comprising the steps of:
  a) providing at least one fertilised egg to at least one egg holder in an egg-growth chamber, the or each egg holder being adapted to retain the at least one fertilized egg and allow passage of the larvae therefrom after hatching;
  b) providing conditions within the egg-growth chamber suitable for the fertilized egg to hatch as larvae wherein after hatching the larvae pass from the egg holder to a food source to provide larvae in the food source;
  c) placing the larvae in the food source in a larval chamber and allowing the larvae to grow and transform into pre-pupae in the food source;
  d) placing the pre-pupae in the food source in a pupation chamber, the pupation chamber being configured to dry the pre-pupae in the food source to provide pupae in a dried food source;
  e) placing the pupae in the dried food source in a release box in which the pupae develop into adult flies, the release box comprising one or more outlets for adult flies to leave the release box;
  f) allowing at least one male adult fly and at least one female adult fly to leave the release box into a breeding chamber;
  g) allowing at least one male adult fly and at least one female adult fly to mate to provide at least one gravid female, wherein the at least one gravid female oviposits at least one fertilised egg in one or more ovipositing racks;
  f) removing at least one fertilised egg from the one or more ovipositing racks;
  g) optionally, repeating steps (a) to (f).

48) The process of Clause 47, wherein the process is carried out using the modular system of any one of Clauses 1 to 46.

49) The process of Clause 47 or Clause 48, wherein the fertilised eggs in the egg holder contain eggs from a single ovipositing rack from the breeding chamber.

50) The process of any one of Clauses 47 to 49, wherein the fertilised eggs in the egg holder contain eggs from a plurality of ovipositing racks from the same breeding chamber.

51) The process of any one of Clauses 47 to 50, wherein the fertilised eggs in the egg holder contain eggs from a plurality of ovipositing racks from different breeding chambers.

52) The process of any one of Clauses 47 to 51, wherein the fertilised eggs in any one of the or each egg holder are all from one to five days, preferably from one to three days old.

53) The process of any one of Clauses 47 to 52, wherein the larval chamber operates on a 'first in first out' sequential processing system of batches of larvae in the food source, wherein each batch of larvae in the food source spends an appropriate length of time in the larval chamber before being placed to the pupation chamber.

54) The process of any one of Clauses 47 to 53, wherein the pupation chamber operates on a 'first in first out' sequential processing system of batches of pre-pupae in the food source, wherein each batch of pre-pupae in the food source spends an appropriate length of time in the pupation chamber before being placed in the release box.

55) The process of any one of Clauses 47 to 54, wherein the release box operates on a 'first in first out' sequential processing system of batches of pupae in the food source, wherein each batch of pupae in the food source spends an appropriate length of time in the release box before being removed.

56) The process of any one of Clauses 47 to 55, wherein the larval chamber, the pupation chamber and/or the release box is a container.

57) The process of Clause 56, wherein the larval chamber, the pupation chamber and/or the release box are the same container.

58) The process of any one of Clauses 47 to 55, wherein the larvae in the food source are within a container that is dimensioned to be placed in one or more discrete positions in the larval chamber, the pupation chamber and/or the release box.

59) The process of Clause 58, wherein the same container is used to sequentially pass from the larval chamber, to the pupation chamber to the release box.

60) The process of any one of Clauses 47 to 59, wherein the food source prior to the pupation chamber has a moisture content in the range of from 60% to 80%.

61) The process of any one of Clauses 47 to 60 wherein the food source after drying in the pupation chamber has a moisture content of less than 60%.

62) The process of any one of Clauses 47 to 61, wherein the pupation chamber is maintained at a relative humidity of from 10% to 20% below that of the larval chamber.

63) The process of any one of Clauses 47 to 62, wherein the process further comprises in step (b) that the larvae are counted as they pass from the egg holder to the food source.

64) The process of Clause 63, wherein the larvae in step (b) are counted, the counting being carried out using the counting system of any one of clauses Clauses 147 to 159.

65) The process of Clause 63 or 64, wherein the larvae in the food source are placed in the larval chamber once a pre-determined number of larvae have been counted.

66) The process of any one of Clauses 47 to 65, wherein the process comprises in step (f) that the adult flies are counted as they pass from the release box to the breeding chamber.

67) The process of Clause 66, wherein the release box is configured to count the number of flies passing therefrom, the release box comprising one or more or all of the features of the release box of Clauses 162 to 176.

68) A modular system for breeding flies, comprising:
an egg-growth chamber in which fertilised eggs develop and hatch as larvae, the egg-growth chamber comprising at least one egg holder, the or each egg holder being adapted to retain the fertilized eggs and allow passage of the larvae therefrom after hatching, wherein the egg-growth chamber further comprises a means to count the larvae released from the egg holder;
a larval chamber configured to receive the larvae in a food source and to permit the larvae to feed on the food source and develop into pre-pupae;
a pupation chamber configured to receive the pre-pupae and to permit the pre-pupae to develop into pupae;
a release box configured to receive pupae and permit the pupae to develop into adult flies, the release box comprising one or more outlets for adult flies; and
a breeding chamber configured to receive adult flies via the outlets in the release box and to permit the adult flies to mate to provide gravid females which oviposit fertilised eggs in one or more ovipositing racks.

69) The modular system of Clause 68, wherein the or each egg holder is positioned such that the larvae drop from the egg holder to contact a surface configured to separate individual larvae.

70) The modular system of Clause 68 or Clause 69, wherein one or more of the egg-growth chamber, larval chamber, pupation chamber, release box and breeding chamber has controlled environmental conditions.

71) The modular system of any one of Clauses 68 to 70, wherein the egg-growth chamber is maintained at a relative humidity of from 60% to 80% and at a temperature in the range of from 25° C. to 32° C.

72) The modular system of any one of Clauses 68 to 71, wherein the larval chamber is maintained at a relative humidity of from 60% to 80% and at a temperature in the range of from 25° C. to 32° C.

73) The modular system of any one of Clauses 68 to 72, wherein the pupation chamber is maintained at a relative humidity of from 20% to 60% and at a temperature in the range of from 25° C. to 32° C.

74) The modular system of any one of Clauses 68 to 73, wherein the release box is maintained at a relative humidity of from 20% to 60% and at a temperature in the range of from 25° C. to 32° C.

75) The modular system of any one of Clauses 68 to 74, wherein the breeding chamber is maintained at a relative humidity of from 60% to 80% and at a temperature in the range of from 25° C. to 32° C.

76) The modular system of any one of Clauses 68 to 75, wherein the larval chamber, the pupation chamber and/or the release box is a container.

77) The modular system of Clause 76, wherein the larval chamber, the pupation chamber and/or the release box are the same container.

78) The modular system of Clause 76 or Clause 77, wherein the pupation chamber and/or the release box further comprises a lid that covers the container.

79) The modular system of Clause 78, wherein the lid comprises the one or more outlets.

80) The modular system of any one of Clauses 68 to 79, wherein the larval chamber has one or more discrete positions for receiving separate batches of larvae in the food source.

81) The modular system of Clause 80, wherein the one or more discrete positions are selected from the group consisting of: shelves; racks; and drawers.

82) The modular system of Clause 80 or Clause 81, wherein the larvae in the food source are within a container that is dimensioned to be placed in one of the one or more discrete position in the larval chamber.

83) The modular system of any one of Clauses 80 to 82, wherein the pupation chamber has one or more discrete positions for receiving different batches of pre-pupae in the food source.

84) The modular system of Clause 83, wherein the one or more discrete positions are selected from the group consisting of: shelves; racks; and drawers.

85) The modular system of Clause 83 or Clause 84, wherein the pre-pupae in the food source are within a container with a lid, wherein the lid covers the container, and wherein the container with lid is dimensioned to be placed in one of the one or more discrete positions in the pupation chamber.

86) The modular system of Clause 85, wherein the lid has perforations for ventilation, the perforations sized to prevent the adult flies leaving the container.

87) The modular system of Clause 85 or Clause 86, wherein the lid has at least one opening which is operable between an open and a closed position, the opening being in a closed position in the pupation chamber.

88) The modular system of any one of Clauses 68 to 87, wherein light is at least partially excluded from the pupation chamber.

89) The modular system of any one of Clauses 68 to 88, wherein the release box has one or more discrete positions for receiving different batches of pupae in the food source.

90) The modular system of Clause 89, wherein the one or more discrete positions are selected from the group consisting of: shelves; racks; and drawers.

91) The modular system of Clause 89 or Clause 90, wherein the pre-pupae in the food source are within a container with a lid, the container and lid dimensioned to be placed in one of the one or more discrete positions in the release box.

92) The modular system of Clause 91, wherein the lid has perforations for ventilation sized to prevent the adult flies leaving the container.

93) The modular system of Clause 91 or Clause 92, wherein the lid has an opening which is operable between an open and closed position, the opening being in an open position in the release box.

94) The modular system of any one of Clauses 68 to 93, wherein the larval chamber, the pupation chamber and/or the release box is a container.

95) The modular system of Clause 94, wherein the larval chamber, the pupation chamber and/or the release box are the same container.

96) The modular system of Clause 68 or Clause 93, wherein the larvae in the food source are within a container that is dimensioned to be placed in one or more discrete positions in the larval chamber, the pupation chamber and/or the release box.

97) The modular system of Clause 96, wherein the same container is used to sequentially pass from the larval chamber, to the pupation chamber to the release box.

98) The modular system of any one of Clauses 68 to 97, wherein the pre-pupae are dried in situ in the food source in the pupation chamber.

99) The modular system of any one of Clauses 68 to 98, wherein the food source prior to the pupation chamber has a moisture content in the range of from 60% to 80%.

100) The modular system of any one of Clauses 68 to 99, wherein the food source after drying in the pupation chamber has a moisture content of less than 60%.

101) The modular system of any one of Clauses 68 to 100, wherein the pupation chamber is maintained at a relative humidity of from 10% to 20% below that of the larval chamber.

102) The modular system of any one of Clauses 68 to 101, wherein the means to count the larvae is a system comprising:
   a drop point from where larvae hatching from at least one fertilised egg falls;
   one or more angled surfaces positioned below the drop point such that as the larvae fall from the drop point they contact at least one of the one or more angled surfaces, wherein said contact separates the larvae into individuals and directs the larvae from the one or more angled surfaces;
   wherein a monitoring device is counts the individual larvae directed from the one or more surfaces.

103) The modular system of Clause 102, wherein the drop point is at least one of the one or more egg holders of the egg-growth chamber.

104) The modular system of Clause 102 or Clause 103, wherein the drop point is the end of a conveyor system that has collected larvae from the egg holders of the egg-growth chamber.

105) The modular system of Clause 104, wherein the conveyor system is a conveyor belt.

106) The modular system of any one of Clauses 102 to 105, wherein the distance between the drop point and the one or more angled surfaces is between 50 mm and 400 mm.

107) The modular system of Clause 106, wherein the distance between the drop point and the one or more angled surfaces is between 100 mm and 300 mm.

108) The modular system of any one of Clauses 102 to 107, wherein the angle of the surface with respect to a direction of the larvae as they fall from the drop point is from 30° to 70°.

109) The modular system of any one of Clauses 102 to 108, wherein the distance between the drop point and the one or more angled surfaces is between 100 mm and 300 mm and wherein the angle of the one or more angled surfaces with respect to a substantially vertical direction of the larvae as they fall from the drop point is from 30° to 70°.

110) The modular system of any one of Clauses 102 to 109, wherein the monitoring device is a camera having a field of vision attached to a device capable of visualising and recording the number of larvae falling through its field of vision.

111) The modular system of Clause 110, wherein a screen is provided within the camera's field of vision such that the larvae pass between the camera and the screen.

112) The modular system of Clause 111, wherein the screen is black.

113) The modular system of any one of Clauses 68 to 112, wherein the or each outlet on the release box comprises a counter which counts the number of adult flies leaving the release box and wherein the breeding chamber is adapted to receive a specific number of adult flies from the one or more outlets of the release box.

114) The modular system of Clause 113, wherein the release box comprises:
at least one discrete position for receiving pupae;
one or more outlets for adult flies to leave the release box;
wherein the or each outlet comprises a monitoring device for counting the individual flies leaving the release box.

115) The modular system of Clause 114, wherein the at least one discrete position is a container with a lid.

116) The modular system of Clause 114 or Clause 115, wherein the release box comprises a plurality of discrete positions for receiving pupae.

117) The modular system of Clause 116, wherein the pupae are provided in containers.

118) The modular system of any one of Clauses 114 to 117, wherein the pupae are provided with a food source.

119) The modular system of any one of Clauses 114 to 118, wherein the outlets are partitioned to provide each outlet with multiple smaller openings.

120) The modular system of any one of Clauses 114 to 119, wherein the multiple smaller openings are sized to allow the passage of no more than one individual fly at once.

121) The modular system of Clause 120, wherein each smaller opening has a diameter in the range of 6 mm to 14 mm.

122) The modular system of any one of Clauses 119 to 121, wherein the smaller openings in the release box have a total surface area in the range of from 0.005 cm$^2$ per pupa to 0.03 cm$^2$ per pupa.

123) The modular system of any one of Clauses 119 to 122, wherein each of the openings comprises a monitoring device for counting the individual flies leaving the release box.

124) The modular system of any one of Clauses 114 to 123, wherein the monitoring device detects and counts the flies by one of the group consisting of: breaking a light beam and a charge detector.

125) The modular system of any one of Clauses 114 to 124, wherein the release box is moveable to release flies into more than one breeding chamber.

126) The modular system of Clause 125, wherein the release box is mounted on wheels or rails.

127) The modular system of any one of Clauses 68 to 126, wherein the pre-pupae are dried in situ in the food source in the pupation chamber.

128) A process for breeding flies, comprising the steps of:
a) providing at least one fertilised egg to at least one egg holder in an egg-growth chamber, the or each egg holder being adapted to retain the at least one fertilized egg and allow passage of the larvae therefrom after hatching;
b) providing conditions within the egg-growth chamber suitable for the fertilized egg to hatch as larvae wherein after hatching the larvae pass from the egg holder to a food source;
c) counting the larvae as they pass from the egg holder to the food source using a monitoring device;
d) providing a pre-determined number of counted larvae to a food source;
e) placing the pre-determined number of counted larvae in a food source in a larval chamber and allowing the larvae to grow and transform into pre-pupae;
f) placing the pre-pupae to a pupation chamber and allowing the pre-pupae to transform into pupae;
g) placing the pupae to a release box in which the pupae develop into adult flies, the release box comprising one or more outlets for adult flies to leave the release box;
h) allowing at least one male adult fly and at least one female adult fly to leave the release box into a breeding chamber;
i) allowing at least one male adult fly and at least one female adult fly to mate to provide at least one gravid female, wherein the at least one gravid female oviposits at least one fertilised egg in one or more removable ovipositing racks;
j) removing at least one fertilised egg from the one or more ovipositing racks;
k) optionally, repeating steps (a) to (j).

129) The process of claim 128, wherein, when the larvae pass from the egg holder to the food source they contact a surface configured to separate the larvae into individual larvae.

130) The process of Clause 128 or Clause 129, wherein the process utilises the modular system of any one of Clauses 68 to 127.

131) The process of any one of Clauses 128 to 130, wherein the fertilised eggs in the at least one egg holder contain eggs from a single ovipositing rack from the breeding chamber.

132) The process of any one of Clauses 128 to 131, wherein the fertilised eggs in the at least one egg holder contain eggs from a plurality of ovipositing racks from the same breeding chamber.

133) The process of any one of Clauses 128 to 132, wherein the fertilised eggs in the at least one egg holder contain eggs from a plurality of ovipositing racks from different breeding chambers.

134) The process of any one of Clauses 128 to 133, wherein the fertilised eggs in any one of the or each egg holder are all from one to three days old.

135) The process of any one of Clauses 128 to 134, wherein the larval chamber operates on a 'first in first out' sequential processing system of batches of larvae in the food source, wherein each batch of larvae in the food source spends an appropriate length of time in the larval chamber before being placed in the pupation chamber.

136) The process of any one of Clauses 128 to 135, wherein the pupation chamber operates on a 'first in first out' sequential processing system of batches of pre-pupae in the food source, wherein each batch of pre-pupae in the food source spends an appropriate length of time in the pupation chamber before being placed in the release box.

137) The process of any one of Clauses 128 to 136, wherein the release box operates on a 'first in first out' sequential processing system of batches of pupae in the food source, wherein each batch of pupae in the food source spends an appropriate length of time in the release box before being removed.

138) The process of any one of Clauses 128 to 137, wherein the larval chamber, the pupation chamber and/or the release box is a container.

139) The process of Clause 138, wherein the larval chamber, the pupation chamber and/or the release box are the same container.

140) The process of Clause 138 or Clause 139, wherein the larvae in the food source are within a container that is dimensioned to be placed in one or more discrete positions in the larval chamber, the pupation chamber and/or the release box.

141) The process of Clause 140, wherein the same container is used to sequentially pass from the larval chamber, to the pupation chamber to the release box.

142) The process of any one of Clauses 128 to 141, wherein the food source prior to the pupation chamber has a moisture content in the range of from 60% to 80%.

143) The process of any one of Clauses 128 to 142, wherein the food source is dried in the pupation chamber and after drying in the pupation chamber the food source has a moisture content of less than 60%.

144) The process of any one of Clauses 128 to 143, wherein the pupation chamber is maintained at a relative humidity of from 10% to 20% below that of the larval chamber.

145) The process of any one of Clauses 128 to 144, wherein the counting of larvae in step (d) is carried out using the counting system of any one of clauses 148 to 160.

146) The process of any one of Clauses 128 to 145, wherein the process comprises in step (f) that the adult flies are counted as they pass from the release box to the breeding chamber.

147) The process of Clause 146, wherein the release box is the release box of any one of clauses 163 to 177.

148) An apparatus for counting larvae emerging from fertilized eggs of a fly, the system comprising:
   a drop point from where larvae hatching from at least one fertilised egg falls;
   one or more angled surfaces positioned below the drop point such that as the larvae fall from the drop point they contact at least one of the one or more angled surfaces, wherein said contact separates the larvae into individuals and directs the individual larvae from the one or more angled surfaces;
   a monitoring device for counting the individual larvae directed from the one or more surfaces.

149) The apparatus for counting larvae of Clause 148, wherein the drop point is the at least one of the one or more egg holders of the egg-growth chamber of the modular apparatus of any one of Clauses 1 to 46 or Clauses 68 to 127.

150) The apparatus for counting larvae of Clause 149, wherein the drop point is the end of a conveyor system that has collected larvae from the egg holders of the egg-growth chamber of the modular apparatus of any one of Clauses 1 to 46 or Clauses 68 to 127.

151) The apparatus for counting larvae of Clause 150, wherein the conveyor system is a conveyor belt.

152) The apparatus for counting larvae of any one of Clauses 148 to 151, wherein the distance between the drop point and the surface is between 50 mm and 400 mm.

153) The apparatus for counting larvae of Clause 152, wherein the distance between the drop point and the surface is between 100 mm and 300 mm.

154) The apparatus for counting larvae of any one of Clauses 148 to 153, wherein the angle of the surface with respect to a direction of the larvae as they fall from the drop point is from 30° to 70°.

155) The apparatus for counting larvae of any one of Clauses 148 to 154, wherein the distance between the drop point and the surface is between 100 mm and 300 mm and wherein the angle of the surface with respect to a direction of the larvae as they fall from the drop point is from 30° to 70°.

156) The apparatus for counting larvae of any one of Clauses 148 to 155, wherein the monitoring device is a camera having a field of vision attached to a device capable of visualising and recording the number of larvae falling through the field of vision.

157) The apparatus for counting larvae of Clause 156, wherein a screen is provided opposite the camera such that the larvae pass therebetween.

158) The apparatus for counting larvae of Clause 157, wherein the screen is black.

159) The apparatus for counting larvae of any one of Clauses 148 to 158, wherein the system forms part of the egg growth chamber of the modular system of any one of Clauses 1 to 46 or Clauses 68 to 127.

160) The apparatus for counting larvae of any one of Clauses 148 to 159, wherein the apparatus is used to count the larvae in step (d) of Clause 128 or Clause 129.

161) A method for counting larvae comprising the steps of:
   Providing one or more fertilised eggs;
   Providing conditions suitable to allow the eggs to hatch as larvae; and
   Counting the larvae as after they emerge from the one or more fertilised eggs.

162) The method of counting larvae of Clause 161, wherein the method is carried out using the apparatus of any one of Clauses 148 to 160.

163) A release box in which the pupae develop into adult flies, the release box comprising:
   at least one discrete position for receiving pupae;
   one or more outlets for adult flies to leave the release box;
   wherein the or each outlet comprises a monitoring device for counting the individual flies leaving the release box.

164) The release box of Clause 163, wherein the release box is a container with a lid.

165) The release box of Clause 163, wherein the release box comprises a plurality of discrete positions for receiving pupae.

166) The release box of Clause 165, wherein the pupae are provided in containers.

167) The release box of any one of Clauses 163 to 166, wherein the pupae are provided with a food source.

168) The release box of any one of Clauses 163 to 167, wherein the outlets are partitioned to provide each outlet with multiple smaller openings.

169) The release box of any one of Clauses 163 to 168, wherein the multiple smaller openings are sized to allow the passage of no more than one individual fly at once.

170) The release box of Clause 169, wherein each smaller opening has a diameter in the range of 6 mm to 14 mm.

171) The release box of any one of Clauses 168 to 170, wherein the smaller openings in the release box have a total surface area in the range of from 0.005 $cm^2$ per pupa to 0.03 $cm^2$ per pupa.

172) The release box of any one of Clauses 168 to 171, wherein each of the openings comprises a monitoring device for counting the individual flies leaving the release box.

173) The release box of any one of Clauses 163 to 172, wherein the monitoring device detects and counts the flies by one of the group consisting of: breaking a light beam and a charge detector.

174) The release box of any one of Clauses 163 to 173, wherein the release box is moveable to release flies in more than one position.

175) The release box of Clause 174, wherein the release box is mounted on wheels or runners or rails.

176) The release box of any one of Clauses 163 to 175, wherein the release box is part of the modular apparatus of any one of Clauses 1 to 46 or Clauses 68 to 127.

177) The release box of any one of Clauses 163 to 176, wherein the release box is used in the method of Clause 128 or Clause 129.

178) A method of counting flies entering a breeding chamber, wherein said method comprises:

Providing pupae in a pupation chamber in one or more containers, wherein the or each one or more containers comprises one or more outlets configured to allow adult flies to pass from the release box to the breeding chamber;

Counting flies as they pass through the one or more outlets.

179) The method of counting flies of Clause 178, wherein said method comprises the apparatus of any one of Clauses 1 to 46 or Clauses 68 to 127.

180) The modular system of any one of Clauses 1 to 46 or Clauses 68 to 127 wherein the ovipositing rack and the egg holder are separate components.

181) The modular system of any one of Clauses 1 to 46 or Clauses 68 to 127 wherein the ovipositing rack and the egg holder are the same component.

The invention claimed is:

1. A modular system for breeding flies, comprising:
   an egg-growth chamber in which fertilised eggs develop and hatch as larvae, the egg-growth chamber comprising at least one egg holder, the or each egg holder being adapted to retain the fertilized eggs and allow passage of the larvae therefrom after hatching, wherein the egg-growth chamber further comprises an automated means to count the larvae passing from the egg holder;
   a larval chamber configured to receive the larvae in a food source and to permit the larvae to feed on the food source and develop into pre-pupae;
   a pupation chamber configured to receive the pre-pupae and to permit the pre-pupae to develop into pupae;
   a release box configured to receive pupae and permit the pupae to develop into adult flies, the release box comprising one or more outlets for adult flies; and
   a breeding chamber configured to receive adult flies via the outlets in the release box and to permit the adult flies to mate to provide at least one gravid female which oviposits fertilised eggs in one or more ovipositing racks,
   wherein the or each egg holder is positioned such that the larvae drop from the egg holder to contact a surface configured to separate individual larvae, wherein the individual larvae are directed from the surface to be counted by the automated means.

2. The modular system of claim 1, wherein:
   the larval chamber has one or more discrete positions for receiving separate batches of larvae in the food source;
   the pupation chamber has one or more discrete positions for receiving different batches of pre-pupae in the food source; and/or
   the release box has one or more discrete positions for receiving different batches of pupae in the dried food source.

3. The modular system of claim 2, wherein the one or more discrete positions are selected from the group consisting of: shelves; racks; and drawers.

4. The modular system of claim 1, wherein the pre-pupae are dried in situ in the food source in the pupation chamber.

5. The modular system of claim 1, wherein the food source prior to the pupation chamber has a moisture content in the range of from 60% to 80%.

6. The modular system of claim 1, wherein the food source after drying in the pupation chamber has a moisture content of less than 60%.

7. The modular system of claim 1, wherein the pupation chamber is maintained at a relative humidity of from 10% to 20% below that of the larval chamber.

8. The modular system of claim 1, wherein the automated means to count the larvae is an apparatus comprising:
   a drop point from where larvae hatching from at least one fertilised egg falls;
   one or more angled surfaces positioned below the drop point such that as the larvae fall from the drop point they contact at least one of the one or more angled surfaces, wherein said contact separates the larvae into individuals and directs the individual larvae from the one or more angled surfaces;
   wherein a monitoring device counts the individual larvae directed from the one or more surfaces.

9. The modular system of claim 8, wherein the drop point is at least one of the one or more egg holders of the egg-growth chamber.

10. The modular system of claim 8, wherein the distance between the drop point and the one or more angled surfaces is between 50 mm and 400 mm.

11. The modular system of claim 10, wherein the distance between the drop point and the one or more angled surfaces is between 100 mm and 300 mm.

12. The modular system of claim 8, wherein the angle of the one or more angled surfaces with respect to a substantially vertical direction of the larvae as they fall from the drop point is from 30° to 70°.

13. The modular system of claim 8, wherein the monitoring device is a camera having a field of vision attached to a device capable of visualising and recording the number of larvae falling through its field of vision.

14. The modular system of claim 13, wherein a screen is provided within the camera's field of vision such that the larvae pass between the camera and the screen.

15. The modular system of claim 1, wherein the release box is moveable to release flies into more than one breeding chamber.

16. The modular system of claim 15, wherein the release box is mounted on wheels, runners or rails.

17. A process for breeding flies, comprising the steps of:
   a) providing at least one fertilised egg to at least one egg holder in an egg-growth chamber, the or each egg holder being adapted to retain the at least one fertilized egg and allow passage of the larvae therefrom after hatching, wherein the egg-growth chamber further comprises an automated means to count the larvae passing from the egg holder;
   b) providing conditions within the egg-growth chamber suitable for the fertilized egg to hatch as larvae wherein after hatching the larvae pass from the egg holder to a food source;
   c) counting the larvae using the automated means as they pass from the egg holder to the food source using a monitoring device;
   d) providing a pre-determined number of counted larvae to a food source;
   e) placing the pre-determined number of counted larvae in a food source in a larval chamber and allowing the larvae to grow and transform into pre-pupae;
   f) placing the pre-pupae in a pupation chamber and allowing the pre-pupae to transform into pupae;
   g) placing the pupae in a release box in which the pupae develop into adult flies, the release box comprising one or more outlets for adult flies to leave the release box;
   h) allowing at least one male adult fly and at least one female adult fly to leave the release box into a breeding chamber;
   i) allowing at least one male adult fly and at least one female adult fly to mate to provide at least one gravid female, wherein the at least one gravid female oviposits at least one fertilised egg in one or more removable ovipositing racks;

j) removing at least one fertilised egg from the one or more ovipositing racks;

k) optionally, repeating steps (a) to (j);

wherein the or each egg holder is positioned such that the larvae drop from the egg holder to contact a surface configured to separate individual larvae, wherein the individual larvae are directed from the surface to be counted by the automated means.

18. The process of claim 17, wherein, when the larvae pass from the egg holder to the food source they contact the surface configured to separate the larvae into individual larvae.

19. The process of claim 17, wherein:

the larval chamber operates on a 'first in first out' sequential processing system of batches of larvae in the food source, wherein each batch of larvae in the food source spends an appropriate length of time in the larval chamber before being placed in the pupation chamber;

the pupation chamber operates on a 'first in first out' sequential processing system of batches of pre-pupae in the food source, wherein each batch of pre-pupae in the food source spends an appropriate length of time in the pupation chamber before being placed in the release box; and/or the release box operates on a 'first in first out' sequential processing system of batches of pupae in the food source, wherein each batch of pupae spends an appropriate length of time in the release box before being removed.

20. The process of claim 17, wherein the larval chamber, the pupation chamber and/or the release box is a container.

21. The process of claim 20, wherein the larval chamber, the pupation chamber and/or the release box are the same container.

22. The process of claim 21, wherein the same container is used sequentially as the larval chamber, the pupation chamber and the release box.

23. The process of claim 17, wherein the food source prior to the pupation chamber has a moisture content in the range of from 60% to 80%.

24. The process of claim 17, wherein the food source is dried in the pupation chamber and after drying in the pupation chamber the food source has a moisture content of less than 60%.

* * * * *